(12) United States Patent
Tesfayesus et al.

(10) Patent No.: US 11,654,283 B2
(45) Date of Patent: May 23, 2023

(54) OBSTRUCTIVE SLEEP APNEA PATIENT PROGRAMMER FOR IMPLANTABLE DEVICES

(71) Applicant: Medtronic Xomed, LLC, Jacksonville, FL (US)

(72) Inventors: Wondimeneh Tesfayesus, Mounds View, MN (US); Randal Schulhauser, Phoenix, AZ (US); Avram Scheiner, Vadnais Heights, MN (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 54 days.

(21) Appl. No.: 16/752,390

(22) Filed: Jan. 24, 2020

(65) Prior Publication Data
US 2020/0282213 A1    Sep. 10, 2020

Related U.S. Application Data

(60) Provisional application No. 62/814,398, filed on Mar. 6, 2019.

(51) Int. Cl.
*A61N 1/36* (2006.01)
*A61N 1/372* (2006.01)
(Continued)

(52) U.S. Cl.
CPC .......... *A61N 1/3611* (2013.01); *A61B 5/0004* (2013.01); *A61B 5/0015* (2013.01);
(Continued)

(58) Field of Classification Search
CPC .. A61N 1/3611; A61N 1/025; A61N 1/36003; A61N 1/3601; A61N 1/36078;
(Continued)

(56) References Cited

U.S. PATENT DOCUMENTS

| 4,551,473 A | 11/1985 | Schossow |
| 4,655,213 A | 4/1987 | Rapoport et al. |

(Continued)

FOREIGN PATENT DOCUMENTS

| EP | 3355984 A1 | 8/2018 |
| EP | 3071288 B1 | 11/2018 |

(Continued)

OTHER PUBLICATIONS

PCT Search Report and Written Opinion issued in PCT Application No. PCT/US2020/021242 dated Jun. 29, 2020, 11 pages.
(Continued)

*Primary Examiner* — Erin M Piateski
(74) *Attorney, Agent, or Firm* — Shumaker & Sieffert, P.A.

(57) ABSTRACT

An implantable neurostimulator system including an electrical lead having formed thereon a pair of bipolar electrodes, the electrical lead is configured for placement of the pair of bipolar electrodes proximate protrusor muscles of a patient. The system also includes a pulse generator electrically connected to the electrical lead and configured to deliver electrical energy to the pair of bipolar electrodes, the pulse generator having mounted therein a sensor configured to detect one or more physiological parameters, a memory, a control circuit, and a telemetry circuit. The system also including a communications telemetry module (CTM) in communication with the telemetry circuit and configured to receive a data collected by the sensor and data related to delivery of electrical energy to the bipolar electrodes, and an external programmer in communication with the CTM and configured to display a user interface the data collected by the sensor and data related to delivery of electrical energy to the bipolar electrodes.

18 Claims, 7 Drawing Sheets

(51) Int. Cl.
*A61N 1/02* (2006.01)
*A61F 5/56* (2006.01)
*A61B 5/00* (2006.01)
*A61B 5/024* (2006.01)
*A61B 5/11* (2006.01)
*A61B 7/02* (2006.01)
*A61B 5/389* (2021.01)

(52) U.S. Cl.
CPC .......... *A61B 5/0031* (2013.01); *A61B 5/4818* (2013.01); *A61B 5/7264* (2013.01); *A61F 5/566* (2013.01); *A61N 1/025* (2013.01); *A61N 1/3601* (2013.01); *A61N 1/36003* (2013.01); *A61N 1/36078* (2013.01); *A61N 1/36125* (2013.01); *A61N 1/36139* (2013.01); *A61N 1/37247* (2013.01); *A61N 1/37252* (2013.01); *A61B 5/024* (2013.01); *A61B 5/1116* (2013.01); *A61B 5/389* (2021.01); *A61B 7/023* (2013.01); *A61B 2562/0219* (2013.01); *A61N 1/36175* (2013.01)

(58) Field of Classification Search
CPC ............ A61N 1/36125; A61N 1/36139; A61N 1/37247; A61N 1/37252; A61N 1/36175; A61B 5/0004; A61B 5/0015; A61B 5/0031; A61B 5/4818; A61B 5/7264; A61B 5/389; A61B 5/024; A61B 5/1116; A61B 7/023; A61B 2562/0219; A61F 5/566
USPC .......................................................... 607/42
See application file for complete search history.

(56) References Cited

U.S. PATENT DOCUMENTS

| | | |
|---|---|---|
| 4,989,617 A | 2/1991 | Memberg et al. |
| 5,065,756 A | 11/1991 | Rapoport |
| 5,123,425 A | 6/1992 | Shannon, Jr. et al. |
| 5,146,918 A | 9/1992 | Kallok et al. |
| 5,335,654 A | 8/1994 | Rapoport |
| 5,365,945 A | 11/1994 | Halstrom |
| 5,522,862 A | 6/1996 | Testerman et al. |
| 5,540,733 A | 7/1996 | Testerman et al. |
| 6,041,784 A | 3/2000 | Halstrom |
| 6,044,297 A | 3/2000 | Sheldon et al. |
| 6,161,542 A | 12/2000 | Halstrom |
| 6,251,126 B1 | 6/2001 | Ottenhoff et al. |
| 6,269,269 B1 | 7/2001 | Ottenhoff et al. |
| 6,536,439 B1 | 3/2003 | Palmisano |
| 6,587,725 B1 | 7/2003 | Durand et al. |
| 6,635,021 B1 | 10/2003 | Sullivan et al. |
| 6,666,830 B1 | 12/2003 | Lehrman et al. |
| 6,770,037 B2 | 8/2004 | Sullivan et al. |
| 6,818,665 B2 | 11/2004 | Wennerholm et al. |
| 6,935,335 B1 | 8/2005 | Lehrman et al. |
| 7,004,908 B2 | 2/2006 | Sullivan et al. |
| 7,212,862 B2 | 5/2007 | Park et al. |
| 7,225,021 B1 | 5/2007 | Park et al. |
| 7,311,103 B2 | 12/2007 | Jeppesen |
| 7,322,356 B2 | 1/2008 | Critzer et al. |
| 7,469,698 B1 | 12/2008 | Childers et al. |
| 7,473,227 B2 | 1/2009 | Hsu et al. |
| 7,509,164 B2 | 3/2009 | Jensen et al. |
| 7,520,277 B1 | 4/2009 | Grady |
| 7,540,843 B2 | 6/2009 | Backer |
| 7,672,728 B2 | 3/2010 | Libbus et al. |
| 7,678,058 B2 | 3/2010 | Patangay et al. |
| 7,725,195 B2 | 5/2010 | Lima et al. |
| 7,789,837 B2 | 9/2010 | Lehrman et al. |
| 7,819,823 B2 | 10/2010 | Lehrman et al. |
| 7,926,486 B2 | 4/2011 | Childers |
| 7,937,159 B2 | 5/2011 | Lima et al. |
| 8,187,200 B2 | 5/2012 | Jensen et al. |
| 8,220,457 B2 | 7/2012 | Berthon-Jones et al. |
| 8,220,467 B2 | 7/2012 | Sanders |
| 8,307,831 B2 | 11/2012 | Rousseau |
| 8,333,696 B2 | 12/2012 | Levendowski et al. |
| 8,359,097 B2 | 1/2013 | Alt et al. |
| 8,359,108 B2 | 1/2013 | McCreery |
| 8,413,661 B2 | 4/2013 | Rousseau et al. |
| 8,428,727 B2 | 4/2013 | Bolea et al. |
| 8,486,947 B2 | 7/2013 | Schwartz et al. |
| 8,545,231 B2 | 10/2013 | Lloyd et al. |
| 8,545,416 B1 | 10/2013 | Kayyali et al. |
| 8,561,616 B2 | 10/2013 | Rousseau et al. |
| 8,569,374 B2 | 10/2013 | Veasey |
| 8,644,939 B2 | 2/2014 | Wilson et al. |
| 8,740,805 B2 | 6/2014 | Lehrman et al. |
| 8,753,327 B2 | 6/2014 | Fan |
| 8,781,587 B2 | 7/2014 | Alt et al. |
| 8,783,258 B2 | 7/2014 | Jacobs et al. |
| 8,808,158 B2 | 8/2014 | Harrison et al. |
| 8,813,753 B2 | 8/2014 | Bhat et al. |
| 8,892,205 B2 | 11/2014 | Miller, III et al. |
| 8,925,551 B2 | 1/2015 | Sanders |
| 8,999,658 B2 | 4/2015 | Gozal et al. |
| 9,011,341 B2 | 4/2015 | Jensen et al. |
| 9,072,613 B2 | 7/2015 | Shantha |
| 9,078,634 B2 | 7/2015 | Gonzales et al. |
| 9,095,471 B2 | 8/2015 | Iyer et al. |
| 9,114,256 B2 | 8/2015 | Achhab et al. |
| 9,144,511 B2 | 9/2015 | Rousseau et al. |
| 9,186,504 B2 | 11/2015 | Gross |
| 9,254,219 B2 | 2/2016 | Shantha |
| 9,295,670 B2 | 3/2016 | Fan |
| 9,326,886 B2 | 5/2016 | Rousseau |
| 9,402,563 B2 | 8/2016 | Thakur et al. |
| 9,435,814 B2 | 9/2016 | Gozal et al. |
| 9,492,086 B2 | 11/2016 | Ewers et al. |
| 9,526,652 B2 | 12/2016 | Harrison et al. |
| 9,533,114 B1 | 1/2017 | Kayyali et al. |
| 9,545,331 B2 | 1/2017 | Ingemarsson-Matzen |
| 9,561,012 B2 | 2/2017 | Hirabayashi |
| 9,655,767 B1 | 5/2017 | Harrison et al. |
| 9,662,045 B2 | 5/2017 | Skelton et al. |
| 9,687,383 B2 | 6/2017 | Ingemarsson-Matzen |
| 9,744,354 B2 | 8/2017 | Bolea et al. |
| 9,757,560 B2 | 9/2017 | Papay |
| 9,855,164 B2 | 1/2018 | Weadock et al. |
| 9,883,847 B2 | 2/2018 | Wolf et al. |
| 9,889,299 B2 | 2/2018 | Ni et al. |
| 10,022,262 B2 | 7/2018 | Irwin et al. |
| 10,029,098 B2 | 7/2018 | Papay |
| 10,065,038 B2 | 9/2018 | Papay |
| 10,111,774 B2 | 10/2018 | Gonzales et al. |
| 10,123,900 B2 | 11/2018 | Mohan et al. |
| 10,149,621 B2 | 12/2018 | Yoon et al. |
| 10,166,268 B2 | 1/2019 | Mendelowitz et al. |
| 10,172,920 B2 | 1/2019 | Braley et al. |
| 10,206,571 B2 | 2/2019 | Ewers et al. |
| 10,314,736 B2 | 6/2019 | Catalano |
| 10,368,800 B2 | 8/2019 | Qiu |
| 10,406,306 B2 | 9/2019 | Whiting et al. |
| 10,500,086 B1 | 12/2019 | Harrison et al. |
| 10,543,119 B2 | 1/2020 | Ingemarsson-Matzen |
| 10,569,037 B2 | 2/2020 | O'Day |
| 10,575,981 B2 | 3/2020 | Rayek et al. |
| 10,617,694 B2 | 4/2020 | Hedner et al. |
| 10,632,009 B2 | 4/2020 | Goff et al. |
| 10,675,467 B2 | 6/2020 | Papay |
| 10,744,339 B2 | 8/2020 | Makansi |
| 2008/0103407 A1 | 5/2008 | Bolea et al. |
| 2010/0174341 A1* | 7/2010 | Bolea .................. A61N 1/0556 607/42 |
| 2011/0093032 A1* | 4/2011 | Boggs, II ............. A61N 1/3611 607/42 |
| 2014/0228905 A1* | 8/2014 | Bolea .................. A61N 1/3611 607/42 |
| 2015/0142075 A1 | 5/2015 | Miller, III et al. |
| 2015/0224307 A1 | 8/2015 | Bolea |
| 2016/0354603 A1 | 12/2016 | Keenan et al. |

(56) References Cited

U.S. PATENT DOCUMENTS

| | | |
|---|---|---|
| 2017/0290528 A1* | 10/2017 | Ternes ................. A61B 5/4818 |
| 2017/0296815 A1 | 10/2017 | Papay |
| 2018/0133474 A1 | 5/2018 | Meadows et al. |
| 2019/0000350 A1* | 1/2019 | Narayan .................. A61B 5/08 |
| 2020/0269044 A1 | 8/2020 | Papay |
| 2020/0281763 A1 | 9/2020 | Scheiner |
| 2020/0338358 A1 | 10/2020 | Makansi |
| 2020/0346017 A1 | 11/2020 | Caparso et al. |

FOREIGN PATENT DOCUMENTS

| | | |
|---|---|---|
| WO | 2011016864 A1 | 2/2011 |
| WO | 2017059072 A1 | 4/2017 |
| WO | 2018129280 A1 | 7/2018 |

OTHER PUBLICATIONS

International Preliminary Report on Patentability from International Application No. PCT/US2020/021242, dated Sep. 16, 2021, 8 pp.

* cited by examiner

OBSTRUCTIVE SLEEP APNEA PATIENT PROGRAMMER FOR IMPLANTABLE DEVICES

CROSS-REFERENCE TO RELATED APPLICATION

This application claims priority to U.S. Provisional Application No. 62/814,398 filed Mar. 6, 2019 and entitled INTRAMUSCULAR HYPOGLOSSAL NERVE STIMULATION FOR OBSTRUCTIVE SLEEP APNEA THERAPY, the entire contents of which are incorporated herein by reference.

TECHNICAL FIELD

This disclosure relates to a medical device system and method for therapeutic electrical stimulation of the lingual muscles for treatment of obstructive sleep apnea. More particularly this disclosure is directed to systems and methods for monitoring therapy, analyzing therapy, and improving patient outcomes.

BACKGROUND

Implantable medical devices capable of delivering electrical stimulation pulses have been proposed or are available for treating a variety of medical conditions, such as cardiac arrhythmias and chronic pain as examples. Obstructive sleep apnea (OSA), which encompasses apnea and hypopnea, is a serious disorder in which breathing is irregularly and repeatedly stopped and started during sleep, resulting in disrupted sleep and reducing blood oxygen levels. OSA is caused by complete or partial collapse of the pharynx during sleep. In particular, muscles in a patient's throat intermittently relax thereby obstructing the upper airway while sleeping. Airflow into the upper airway can be obstructed by the tongue or soft pallet moving to the back of the throat and covering a smaller than normal airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems and increased accidents. Additionally, loss of sleep occurs when a person is awakened during an apneic episode. Implantable medical devices capable of delivering electrical stimulation pulses have been proposed for treating OSA by electrically stimulating muscles around the upper airway that may block the airway during sleep.

SUMMARY

One aspect of the disclosure is directed to an implantable neurostimulator (INS) system including: an electrical lead having formed thereon a pair of bipolar electrodes, where the electrical lead is configured for placement of the pair of bipolar electrodes proximate protrusor muscles of a patient; a pulse generator electrically connected to the electrical lead and configured to deliver electrical energy to the pair of bipolar electrodes, the pulse generator having mounted therein a sensor configured to detect one or more physiological parameters, a memory, a control circuit, and a telemetry circuit; a communications telemetry module (CTM) in communication with the telemetry circuit and configured to receive a data collected by the sensor and data related to delivery of electrical energy to the bipolar electrodes; and an external programmer in communication with the CTM and configured to display a user interface the data collected by the sensor and data related to delivery of electrical energy to the bipolar electrodes.

Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The system where the user interface displayable on the external programmer is configured to receive an input from a user to initiate therapy delivery. The system where the user interface displayable on the external programmer is configured to display an amount of therapy delivered by the electrodes. The system further including an artificial intelligence (AI) engine configured to analyze the data collected by the sensor and data related to delivery of electrical energy to the bipolar electrodes. The system where the AI is configured to analyze the data collected by the sensor and data related to delivery of electrical energy to the bipolar electrodes and adjust a therapy delivery program stored in the memory for the delivery of the electrical energy to the bipolar electrodes. The system where the AI is configured to analyze electromyograph (EMG) data collected by the sensor to determine a tonal state of the protrusor muscles of the patient. The system where based on the determination of the tonal state of the protrusor muscles, the AI communicates with the control circuit to initiate delivery of electrical energy to the bipolar electrodes. The system where the sensor data includes one or more of motion data, heart rate data, electrocardiogram data, respiration rate data, electromyograph data, blood-oxygen saturation data or posture data. The system where the AI is configured to calculate one or more of an apnea-hypopnea index (AHI) value, a respiration disturbance index (RDI) value, total sleep time, sleep efficiency value, power consumption value, therapeutic efficiency. The system further including one or more external sensors in communication with the CTM. The system further including a server in communication with the external programmer or an external sensor and configured to receive the data collected by the sensor, data related to delivery of electrical energy to the bipolar electrodes, and data collected by the external sensor. The system where the data collected by the sensor, data related to delivery of electrical energy to the bipolar electrodes, and data collected by the external sensor are stored in an electronic medical record (EMR) for the patient. The system further including an AI with access to the EMR and configured to analyze the data contained therein to update a therapy delivery program for delivery of delivery of electrical energy to the bipolar electrodes. The system where the sensor data stored in the EMR includes one or more of motion data, heart rate data, electrocardiogram data, respiration rate data, electromyograph data, blood-oxygen saturation data or posture data. The system where the AI is configured to calculate one or more of an apnea-hypopnea index (AHI) value, a respiration disturbance index (RDI) value, total sleep time, sleep efficiency value, power consumption value, therapeutic efficiency. The system where the server is configured to communicate the updated therapy delivery program to the external programmer, the external programmer configured to communicate the updated therapy delivery program to the memory of the pulse generator. The system further including a remote computer in communication with the server, where the remote computer include a user interface displaying the data collected by the sensor, data related to delivery of electrical energy to the bipolar electrodes, and data collected by the external sensor. The system where the remote computer is configured to receive and permit review of an updated therapy delivery program. The system where the AI has access to EMR data of a larger population of patients. The system where the AI is configured to analyze the EMR data of the larger population and identify one or more parameters for adjustment in a therapy delivery program for the delivery of electrical energy to the pair of bipolar electrodes, therapy delivery program being stored in the memory in the pulse generator.

Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

DETAILED DESCRIPTION

Figure 1:
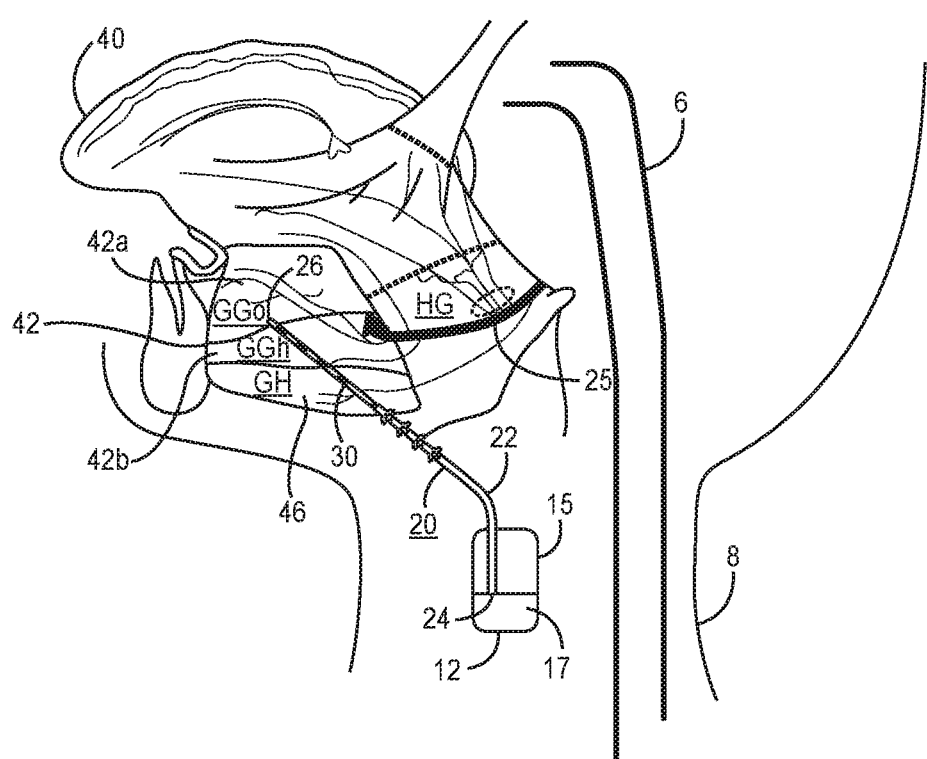
FIG. 1 is a conceptual diagram of an implantable neurostimulator (INS) for delivering OSA therapy.

A medical device system for delivering electrical stimulation to the lingual muscles of the tongue, specifically the protrusor muscles, for the treatment of OSA is described herein. Electrical stimulation is delivered to cause the tongue of a patient to be in a protruded state, during sleep, to avoid or reduce upper airway collapse and obstruction. As used herein, the term, "protruded state" with regard to the tongue refers to a position that is moved forward and/or downward compared to the non-stimulated position or a relaxed position. Those of skill in the art will recognize that to be in a protruded state does not require the tongue to be coming out of the mouth of the patient, indeed it is preferable that the tongue not extend out of the mouth of the patient, but only be advanced forward to a point where obstruction of the airway is mitigated or eliminated. The protruded state is a state associated with the recruitment of protrusor muscles of the tongue (also sometimes referred to as "protruder" muscles of the tongue) including the genioglossus and geniohyoid muscles. A protruded state is the opposite of a retracted and/or elevated position associated with the recruitment of the retractor muscles, e.g., styloglossus and hyoglossus muscles, which retract and elevate the tongue. Electrical stimulation is delivered to cause the tongue to move to and maintain a protruded state to prevent collapse, open or widen the upper airway of a patient to promote unrestricted or at least reduced restriction of airflow during breathing.

Electrical stimulation systems, as described in greater detail below, include an external programmer that communicates with an implanted device. This external programmer, whether they be for pacemakers, an implantable cardiac defibrillators (ICD), or cardiac resynchronization therapy (CRT) devices or a brain implantation for deep brain stimulation (DBS), are used to collect certain data from the implanted device, and to update the stimulation, defibrillation, and other parameters of the implantable device. However, most of these devices are constantly on and monitoring the conditions they are to treat and can apply therapy on an as needed basis that can be determined by logical circuits within the implanted device. Thus, there is no need or even ability for the patient to start or end therapy. The patient may have the opportunity to adjust therapy within a small window of options, but any significant changes are best left to the health care provider.

In contrast, implanted OSA therapy devices only need to be engaged when the patient is sleeping. Current systems enable the turning on and off the implanted OAS therapy devices using a communications telemetry module (CTM). One aspect of the disclosure is directed to improvements to the CTM and integration with the external programmer enhancing functionality of the CTM and enhancing the patient experience.

A further aspect of the disclosure is directed to the use of artificial intelligence (AI) resident on the CTM to execute algorithms and analyze data generated by the implanted OSA therapy devices. The analysis can provide guidance on the adjustment of the therapy provided to the individual patient when incorporated into the CTM with a shortened feedback loop. Additionally or alternatively, the AI can be incorporated as part of a downstream communication loop and analyze data from a larger population of patients. These AI may be resident on one or more servers, (e.g., cloud based) and can analyze the data from thousands of patients to identify adjustments to therapy that may be of assistance to a particular patient based on improved outcomes of other similarly situated patients.

In conjunction with the above, the patient programmer and CTM provide opportunities to recover and analyze data from the implanted OSA therapy device. The data can be utilized to assess the efficacy of the therapy. In addition, the integrity of the implantable OSA therapy device may be assessed. Further, alterations to improve the therapy can be considered by health care providers and communicated to the patient programmer and CTM for acceptance and updating of the implanted OAS therapy device. These and other aspect are described in greater detail below.

FIG. 1 is a conceptual diagram of implanted OSA therapy device, specifically FIG. 1 depicts an implantable neurostimulator (INS) system for delivering OSA therapy. The INS system 10 includes at least one electrical lead 20 and a pulse generator 12. Pulse generator 12 includes a housing 15 enclosing circuitry including a control circuit, therapy delivery circuit, a sensor, a battery, and telemetry circuit as described below in conjunction with FIG. 2. A connector assembly 17 is hermetically sealed to housing 15 and includes one or more connector bores for receiving at least one medical electrical lead used for delivering OSA therapy and, in some examples, for sensing physiological conditions such as electromyogram (EMG) signals and the like. As depicted in FIG. 1 the pulse generator 12 is implanted in the neck of the patient 8. The instant disclosure is not so limited, and the pulse generator 12 may be located in other locations such as in the chest area or other areas known to those of skill in the art.

Lead 20 includes a flexible, elongate lead body 22 that extends from a lead proximal end 24 to a lead distal end 26. At least two electrodes 30 are carried along a lead distal portion adjacent lead distal end 26 that are configured for insertion within the protrusor muscles 42a, 42b and 46 of the patient's tongue 40. The electrodes 30 are configured for implantation within soft tissue such as musculature proximate to the medial branches of one or both hypoglossal nerves (HGN) that innervate the protrusor muscles of the tongue. The electrodes may be placed approximately 5 mm (e.g., from 2 mm to 8 mm) from a major trunk of the HGN. As such, the electrodes 30 may be referred to herein as "intramuscular electrodes," in contrast to an electrode that is placed on or along a nerve trunk or branch, such as a cuff electrode, used to directly stimulate the nerve trunk or branch. Lead 20 may be referred to herein as an "intramuscular lead" since the lead distal end and electrodes 30 are configured for advancement through the soft tissue, which may include the protrusor muscle tissue, to anchor electrodes 30 in proximity of the HGN branches that innervate the protrusor muscles 42a, 42b and 46. The term "intramuscular" with regard to electrodes 30 and lead 20 is not intended to be limiting, however, since the electrodes 30 may be implanted in connective tissue or other soft tissue proximate the medial HGN and its branches. One or more electrodes 30 may be placed in an area of protrusor muscles 42a, 42b and 46 that include motor points, where each nerve axon terminates in the muscle (also called the neuro-muscular junction). The motor points are not at one location but spread out in the protrusor muscles. Leads 20 may be implanted such that one or more electrodes 30 may be generally in the area of the motor points (e.g., such that the motor points are within 1 to 10 mm from one or more electrodes 30).

The protrusor muscles are activated by electrical stimulation pulses generated by pulse generator 12 and delivered via the intramuscular electrodes 30 to move tongue 40 forward, to promote a reduction in obstruction or narrowing of the upper airway 6 during sleep. As used herein, the term "activated" with regard to the electrical stimulation of the protrusor muscles refers to electrical situation that causes depolarization or an action potential of the cells of the nerve (e.g., hypoglossal nerve(s)) innervating the protrusor muscles and motor points and subsequent depolarization and mechanical contraction of the protrusor muscle cells. In some cases, the muscles may be activated directly by the electrical stimulation pulses. The protrusor muscles that may be activated by stimulation via intramuscular electrodes 30 may include at least one or both of the right and/or left genioglossus muscle (GG) 42, which includes the oblique compartment (GGo) 42a and the horizontal compartment (GGh) 42b (referred to collectively as GG 42) and/or the right and/or left geniohyoid muscle (GH) 46. The GG muscle and GH muscle are innervated by a medial branch of the HGN (also referred to as the XIIth cranial nerve), while the hyoglossus and styloglossus muscles, which cause retraction and elevation of the tongue, are innervated by a lateral branch of the HGN.

The multiple distal electrodes 30 may be used to deliver bilateral or unilateral stimulation to the GG 42 and/or the GH 46 muscles via the medial branch of the HGN or branches thereof, also referred to herein as the "medial HGN." Distal electrodes 30 may be switchably coupled to output circuitry of pulse generator 12 to enable delivery of electrical stimulation pulses in a manner that selectively activates the right and left protrusor muscles in a cyclical or alternating pattern to avoid muscle fatigue while maintaining upper airway patency. Additionally or alternatively, electrical stimulation may be delivered to selectively activate the GG 42 and/or GH 46 muscles or portions thereof during unilateral stimulation of the left or right protrusor muscles.

The lead proximal end 24 includes a connector (not shown in FIG. 1) that is coupleable to connector assembly 17 of pulse generator 12 to provide electrical connection between circuitry enclosed by the housing 15 of pulse generator 12, e.g., including therapy delivery circuitry and control circuitry as described below in conjunction with FIG. 2. The lead body 22 encloses electrical conductors extending from each of the distal electrodes 30 to the proximal connector at proximal end 24 to provide electrical connection between output circuitry of pulse generator 12 and the electrodes 30.

Figure 2:
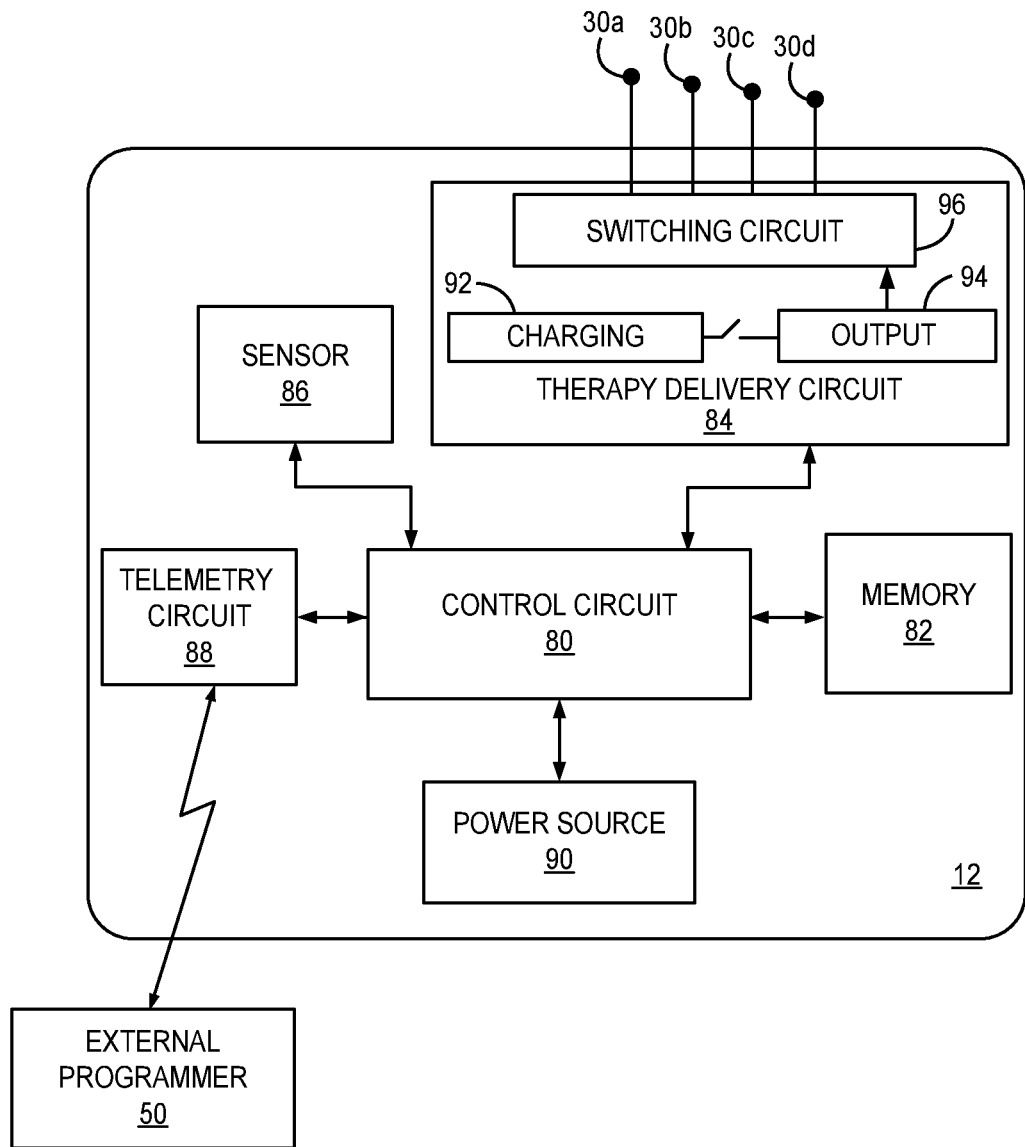
FIG. 2 is a conceptual diagram of a pulse generator included in INS of FIG. 1.

FIG. 2 is a schematic diagram of pulse generator 12. Pulse generator 12 includes a control circuit 80, memory 82, therapy delivery circuit 84, a sensor 86, telemetry circuit 88 and power source 90. Power source 90 may include one or more rechargeable or non-rechargeable batteries for supplying electrical current to each of the control circuit 80, memory 82, therapy delivery circuit 84, sensor 86 and telemetry circuit 88. While power source 90 is shown in communication only with control circuit 80 for the sake of clarity, it is to be understood that power source 90 provides power as needed to each of the circuits and components of pulse generator 12 as needed. For example, power source 90 provides power to therapy delivery circuit 84 for generating electrical stimulation pulses.

The functional blocks shown in FIG. 2 represent functionality included in a pulse generator configured to delivery an OSA therapy and may include any discrete and/or integrated electronic circuit components that implement analog and/or digital circuits capable of producing the functions attributed to a pulse generator herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern medical device system, given the disclosure herein, is within the abilities of one of skill in the art.

Control circuit 80 communicates, e.g., via a data bus, with memory 82, therapy delivery circuit 84, telemetry circuit 88 and sensor 86 (when included) to control OSA therapy delivery and other pulse generator functions. As disclosed herein, control circuit 80 may pass control signals to therapy delivery circuit 84 to cause therapy delivery circuit 84 to deliver electrical stimulation pulses via electrodes 30 according to a therapy protocol that may include selective stimulation patterns of right and left portions of the GG and GH muscles and/or proximal and distal portions of the GG and GH muscles. Control circuit 80 may further be configured to pass therapy control signals to therapy delivery circuit 84 including stimulation pulse amplitude, stimulation pulse width, stimulation pulse number and frequency of a stimulation pulse train.

Memory 82 may store instructions for execution by a processor included in control circuit 80, stimulation control parameters, and other device-related or patient-related data. Control circuit 80 may retrieve therapy delivery control parameters and a therapy delivery protocol from memory 82 to enable control circuit 80 to pass control signals to therapy delivery circuit 84 for controlling the OSA therapy. Memory 82 may store historical data relating to therapy delivery for retrieval by a user via telemetry circuit 88. Therapy delivery data or information stored in memory 82 may include therapy control parameters used to deliver stimulation pulses as well as delivered therapy protocol(s), hours of therapy delivery or the like. When sensor 86 is included, patient related data determined from a sensor signal may be stored in memory 82 for retrieval by a user.

Therapy delivery circuit 84 may include a charging circuit 92, an output circuit 94, and a switching circuit 96. Charging circuit 92 may include one or more holding capacitors that are charged using a multiple of the battery voltage of power source 90, for example. The holding capacitors are switchably connected to output circuit 94, which may include one or more output capacitors that are coupled to a selected bipolar electrode pair via switching circuit 96. The holding capacitor(s) are charged to a programmed pacing pulse voltage amplitude by charging circuit 92 and discharged across the output capacitor for a programmed pulse width. Charging circuit 92 may include capacitor charge pumps or an amplifier for the charge source to enable rapid recharging of holding capacitors included in charging circuit 92. Therapy delivery circuit 84 responds to control signals from control circuit 80 for generating and delivering trains of pulses to produce sustained tetanic contraction of the GG and/or GH muscles or portions thereof to move the tongue forward and avoid upper airway obstruction.

Output circuit 94 may be selectively coupled to bipolar pairs of electrodes 30a-30d via switching circuit 96. Switching circuit 96 may include one or more switches activated by timing signals received from control circuit 80. Electrodes 30a-30d may be selectively coupled to output circuit 94 in a time-varying manner to deliver stimulation to different portions of the protrusor muscles at different time to avoid fatigue, without requiring stimulation to be withheld completely. Switching circuit 96 may include a switch array, switch matrix, multiplexer, or any other type of switching device(s) suitable to selectively couple therapy delivery circuit 84 to bipolar electrode pairs selected from electrodes 30. Bipolar electrode pairs may be selected one at a time or may be selected two or more at time to allow overlapping stimulation of two or more different portions of the protrusor muscles. Overlapping stimulation times of two portions of the protrusor muscles, for example left and right or proximal and distal may maintain a forward position of the tongue and allow a ramping up and ramping down of the electrical stimulation being delivered to two different portions of the protrusor muscles.

Telemetry circuit 88 enables bidirectional communication with an external programmer 50. A user, such as the patient 8, may manually adjust therapy control parameter settings, e.g., as described in Medtronic's Patient Programmer Model 37642, incorporated by reference in its entirety. The patient may make limited programming changes such as small changes in stimulation pulse amplitude and pulse width. A patient programmer 50 is generally accessible to patient 12 and, in many cases, may be a portable device that may accompany the patient throughout the patient's daily routine.

In other examples, a user, such as a clinician, may interact with a user interface of an external programmer 50 to program pulse generator 12 according to a desired OSA therapy protocol. For example, a Physician Programmer Model 8840 available from Medtronic, Inc., Minneapolis, Minn., may be used by the physician to program pulse generator 12 for delivering electrical stimulation. External programmer 50 may be characterized as a physician or clinician programmer if it is primarily intended for use by a physician or clinician.

Programming of pulse generator 12 may refer generally to the generation and transfer of commands, programs, or other information to control the operation of pulse generator 12. For example, external programmer 50 may transmit programs, parameter adjustments, program selections, group selections, or other information to control the operation of pulse generator 12, e.g., by wireless telemetry. As one example, external programmer 50 may transmit parameter adjustments to support therapy changes. As another example, a user may select programs or program groups. A program may be characterized by an electrode combination, electrode polarities, voltage or current amplitude, pulse width, pulse rate, therapy duration, and/or pattern of electrode selection for delivering patterns of alternating portions of the protrusor muscles that are being stimulated. A group may be characterized by multiple programs that are delivered simultaneously or on an interleaved or rotating basis. These programs may adjust output parameters or turn the therapy on or off at different time intervals.

Whether a patient programmer or a physician programmer, the external programmer 50 often communicates with the INS 10 via a Communications Telemetry Module (CTM). The CTM often has a form that is similar in size to a smartphone. The CTM typically includes circuitry for receiving encrypted BLUETOOTH® communications from the external programmer 50 and translating the received signals to a proprietary communication protocol for communication with the INS 10. The CTM can also receive the proprietary communication signals from the INS 10 and translate them encrypted BLUETOOTH® communications for delivery to the external programmer 50. In this manner, updated programs programming for the INS 10 can be regularly updated remotely and pushed to the external programmer 50 without concerns regarding the update interfering with the INS 10. The actual updating of the programs on the INS 10 can then await actions by the patient or physician and ensure that they are occurring at a desired time or when under observation by a health care provider. Further, the CTM may return some information regarding the operation of the INS 10 to the external programmer 50 (e.g., amount of therapy delivered, patient compliance, battery health) as described in greater detail below.

While the use of the CTM has benefits, it also has some drawbacks in that it represents a second device nearly the size of a smartphone. This second device must be held up to the patient's chest, near the implantable device while the patient or physician manipulates the external programmer 50. This can be challenging for some patients and leaves them with only one hand for the manipulation of the external programmer 50.

Figure 3:
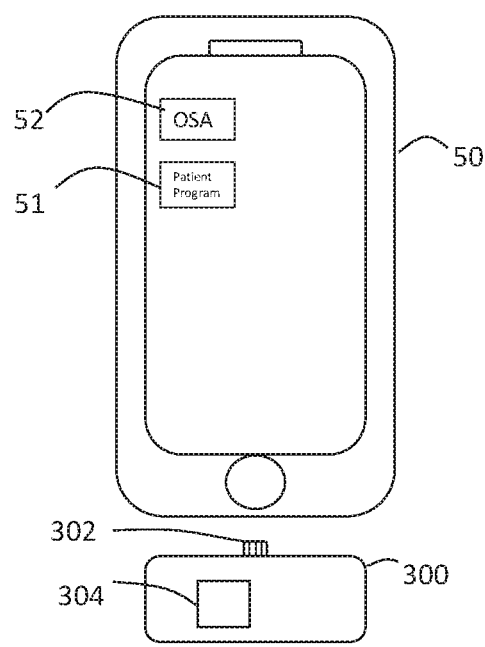
FIG. 3 is a conceptual diagram of an external programmer in accordance with an aspect of the disclosure.

FIG. 3 depicts an aspect of the disclosure related to the external programmer 50 and a CTM 300, which addresses some of these issues. As shown in FIG. 3, the external programmer 50 is embodied on a smartphone. The smart phone may include one or more applications running thereon and displayed as thumbnails 51. In contrast to the system described above, the CTM 300 is configured as a dongle that can be mated with the external programmer 50 via a connector 302. The external programmer 50 and the CTM 502 communicate using the connector 302 on the CTM 300 which is inserted into the smartphone charging port (not shown). The connector 302 may be for example a "Lightning Connector" as used on APPLE® products, a USB Type C connector as used by Android smartphones, micro-USB, and others without departing from the scope of the disclosure. The communications between the external programmer 50 and the CTM 300 may still be encrypted but need not be wirelessly transmitted to the CTM 300. The CTM 300 communicates with the INS 10 via a proprietary communications protocol, as described above.

Figure 4:
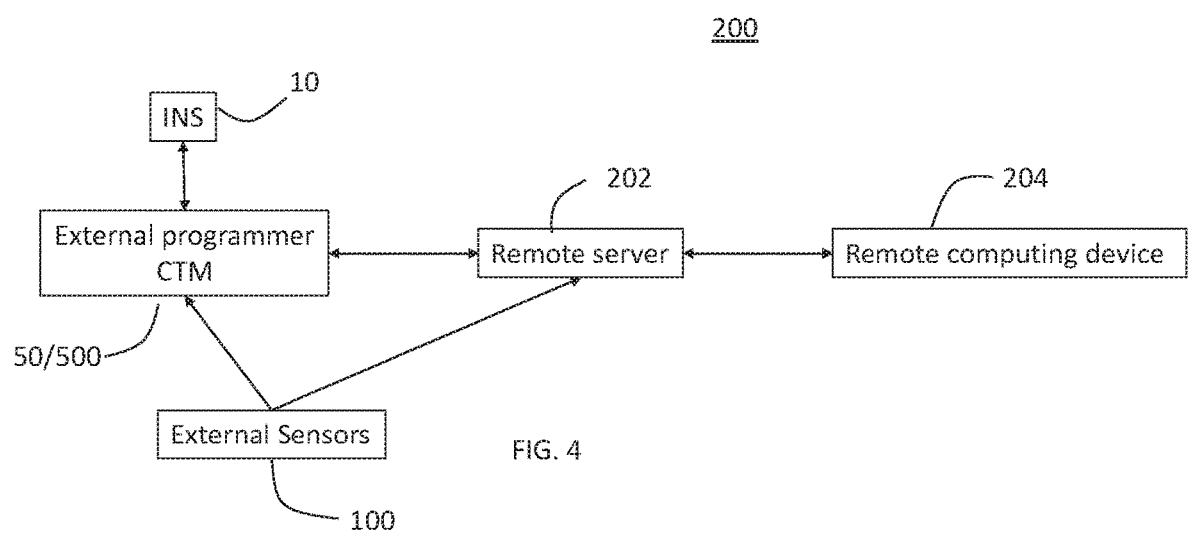
FIG. 4 is a schematic diagram of a communications network in accordance with the disclosure.

FIG. 4 provides a simplified schematic of a communication network 200. The network includes the INS 10, which communicates with the external programmer 50 and CTM 300. External sensors 100 can communicate either with the external programmer 50 and CTM 300 or a remote server 202. The remote server 202 is in bi-directional communication with the external programmer 50 and CTM 300 as well as a remote computing device 204. The remote communicating device may be any type of computing device capable of connecting with the server via a network such as the internet.

To provide updated programming of the INS 10 a user may select the thumbnail 51 for a Patient Program App. This application is in communication with one or more servers 202 (FIG. 4) and may be periodically provided with updated programming for the INS. Launching the Patient Program App. can initiate a communication with the server 202 to confirm that the external programmer 50 has received the latest updated therapy delivery program for the INS 10. If the external programmer 50 has not received the most updated program, software, firmware, or another update, the patient programmer 50 can initiate the necessary download from the server 202. Those of skill in the art will understand that in addition to instances as described above where the update is pulled from the server 202, the server 202 may periodically push updates to the external programmer 50. These updates may be periodically scheduled and managed by the external programmer 50 to occur at times when neither the external programmer 50 nor the CTM 300 is in use by the patient. In addition, the external programmer 50 may receive announcements from the server 202 that can be displayed to the patient indicating that a new program is available for download. A user interface on the external programmer 50 may present a series of screens, menus and dropdowns, enabling the patient to select a variety of actions including updating the available programming and others.

Once the updated therapy delivery program is confirmed available for communication to the INS 10, the external programmer 50 communicates to CTM 300 which initiates wireless communication with the INS 10 via the telemetry circuit 88. The communication with the INS 10 updates the therapy delivery program stored in the memory 82 and executed by the pulse generator 12 for stimulation of the protrusor muscles, as described above.

The communication with the INS 10 also allows for certain data stored in the memory 82 of the pulse generator 12 to be transmitted to the CTM 300 for passage on to the external programmer 50, and where appropriate the server 202. On the patient programmer 50, the patient may review some of the data transmitted from the pulse generator 12 on a user interface. This data may include the current settings of the INS 10 such as frequency of pulsing, pulse width, as well as some data about the INS 10 such as the battery condition, the current version of the therapy delivery program and other data about the INS 10.

As can be seen in FIG. 3, the external programmer 50 includes a second application thumbnail 52 for the OSA App. The OSA App. when selected by the patient may in its simplest form present a patient with a very basic user-interface. That user interface may simply be presenting a patient with a query whether they wish to start INS therapy application. This may be a "yes", "no" inquiry. If "yes" is selected the OSA App. initiates a communication with the CTM 300, and a communication is sent to telemetry circuit 88 and control circuit 80. The control circuit 80 may then read out a therapy delivery program stored in the memory 82 and based on the therapy delivery program, signals will be sent to the therapy delivery circuit 84 to generate and deliver stimulation pulses to distal electrodes 30a-30d and provide the therapy to the patient. Accordingly, in order to initiate therapy delivery of the INS 10, the CTM 300 must be in proximity of the patient and INS 10 such that the communications described above between the CTM 300 and the INS 10 can take place.

Though the CTM 300 is described generally herein as being a dongle configuration that is connected to the external programmer 50, the instant disclosure is not so limited, and these two components could be combined into a single platform similar to the smartphone depicted as the external programmer 50 in FIG. 3.

As will be appreciated, the program stored in the memory 82, may include a delay period before initiating therapy and the delivery of stimulation pulses. This delay will allow the patient to complete their routine and to fall asleep before therapy commences. Another feature of the user interface of the OSA App. is the ability for the patient to adjust certain aspects of the therapy delivery program. One such aspect that may be adjusted by the patient is the delay period before initiating therapy. Accordingly, the patient may adjust the delay period via the OSA App., and that update to the therapy delivery program can be transmitted to the INS 10 and stored in the memory 82. Thus, in accordance with the disclosure, the patient cannot only initiate therapy but can control aspects of the therapy delivery.

Receiving feedback from and control of operation of the INS 10 are utilizing the CTM 300 and the sensor 86 are further aspects of the disclosure. In an initial aspect, the INS 10 can send to the CTM data regarding the duration of therapy applied, the magnitude of the therapy applied, and other data regarding the INS 10 and how therapy has been applied to the patient.

In addition to the operational data that can be returned to the CTM 300 and ultimately the server 200 a variety of sensor data signifying various physiological data of the patient can also be received by the CTM 300. These sensors may include one or accelerometers, inertial measurement units (IMU), fiber-Bragg gratings (e.g., shape sensors), optical sensors, acoustic sensors, and others without departing from the scope of the disclosure. The sensor 86, which may of course be any number of separate sensors, may take many different forms and provide a variety of different data for analysis. For example, the sensor 86 may be a blood-oxygen saturation sensor. This may be an optical sensor and configured as either a reflectance blood-oxygen saturation sensor or a transmissive blood-oxygen saturation sensor. In the case of the transmissive blood-oxygen sensor a light source may be formed as part of a cuff designed to surround a blood vessel. A photodetector may be configured on an opposite side of the cuff from the light source. Other configurations of the blood-oxygen saturation sensor either within a body of the pulse generator 12 or operably connected there are also considered within the scope of the disclosure. Indeed, in accordance with the disclosure, the blood-oxygen saturation sensor may be entirely separate from the INS 10 and simply an external sensor applied to the finger of the patient, but in communication with the external programmer 50.

A further sensor 86 may be a motion detector. The motion detector may be an accelerometer, for example a three-axis accelerometer. This motion detector may be tuned to detect motion caused by movement of the patient (e.g., motion caused by the beating of the heart, or motion caused by respiration and others). Further, the sensor 86 may be tuned to detect movement of the patient's legs. In accordance with one aspect of the disclosure leg motion data might be detected by sensing motion that is inconsistent with motion caused by the patient's heartbeat or respiration and does not result in a change in posture (described below) of the patient. The detection of the motion caused by the heart can provide pulse or heart rate data. The detection of the motion caused by respiration can provide respiration rate data, as well as identifying instances where the respiration is interrupted, as it is during an apnea. Still further, the three-axis accelerometer may be tuned to detect snoring. Band pass filtering can be employed to remove all but the appropriate frequency input that is associated with heat beat, respiration, snoring, etc. In another aspect of the sensor 50, a three-axis accelerometer acts, as noted above, as a motion detector.

As mentioned above, sensor 86 may be a posture detector. As a posture detector, such as one configured from a three-axis accelerometer can be employed to detect when the patient is in a reclined or sleeping position and even whether the patient is laying prone or supine or laying on their right or left sides. The effect of 1 G of gravitational acceleration applied directly along an axis of a stationary accelerometer provides a characteristic output voltage signal having an amplitude that can be referenced or scaled as +1 for angular computation purposes. The effect of 1 G of gravitational acceleration applied in precisely the opposite or negative direction to the sensitive axis provides a characteristic output voltage signal amplitude that is referenced or scaled as −1. If the axis is oriented transverse to the direction of the gravitational force, a bias voltage level output signal should be present, and that voltage signal level is referenced or scaled as 0. The degree to which the axis is oriented away or tilted from the direction of the gravitational force can also be detected by the magnitude and polarity of the output voltage signal level deviating from the bias level scaled to 0 and below the output signal level values scaled to +1 and −1. Other scales may be employed, depending on the signal polarities and ranges employed. The sensor 86 may include its own microprocessor with autocalibration of offset error and drift (possibly caused by temperature variation or other things).

TABLE 1

| Posture | $a_x$ | $a_y$ | $a_z$ |
|---|---|---|---|
| UP | 0 | +1 | 0 |
| SUPINE | 0 | 0 | +1 |
| PRONE | 0 | 0 | −1 |
| RIGHT | −1 | 0 | 0 |
| LEFT | +1 | 0 | 0 |

Table 12 sets forth the ideal, scaled amplitudes of the output signals, $a_x$, $a_y$, and $a_z$, respectively, of a three-axis accelerometer employed in sensor 50 and incorporating into implantable device 10. (The units in the ideal example would be in gravity or "g"). One axis of the accelerometer ($a_y$) is aligned to earth's gravitational field when INS 10 is implanted. Thus, when standing upright and remaining still, the amplitude or level of the output signal $a_y$ of three-axis accelerometer should be at +1. In this orientation, the scaled amplitudes of the output signals $a_z$ and $a_x$ of the three-axis accelerometer, respectively, should approach 0.

The scaled amplitude of the output signal $a_z$ of the three-axis accelerometer should approach +1 or −1, respectively, when the patient lies still and is either supine or prone on their back or stomach and if the INS 10 is implanted with the z-axis of the three axis accelerometer aligned in a posterior-anterior position. In these positions, the amplitudes of the output signals $a_y$ and $a_x$ of the three-axis accelerometer, respectively, should approach 0. In the same fashion, the patient lying on the right and left sides will orient the sensitive axis of the three-axis accelerometer with earth's gravitational field to develop the scaled amplitude of either −1 or +1 of the output signal $a_x$. The amplitudes of the output signals $a_y$ and $a_z$ of the three-axis accelerometer should approach 0. In these ideal orientations of Table 1, there is no rotation of the axes of the INS 10 with respect to earth's gravitational field.

As will be appreciated, the determination described above identifies the pose of the INS 10 and not necessarily the patient in which it is implanted. In practice the INS 10 will rarely if ever be implanted in the patient such that the three axes of the three-axis accelerometer precisely align the idea orientations of Table 1. Accordingly, following implantation of the INS 10, a series of calibration tests can be undertaken during which the patient is alternated from standing to lying, from prone to supine, and from right to left sides. By acquiring a series of such values, the sensor 86 can be calibrated for the implantation, to determine the voltage output values of each of the three axes of the accelerometer in each of the positions. Further, though not described in detail herein, similar analyses may be undertaken to determine when a person is in a slightly reclined position such as when sitting in an airplane seat or other position.

The sensor 86 may be an electrocardiogram (ECG) sensor. An ECG is a recording of the electrical activity of the heart over a period of time. While an ECG typically employs sensors placed on the skin, an effective ECG can be employed in an implantable device (e.g., INS 10) wherein at least two electrodes, separated by a distance (e.g., at least about 35 mm), are employed to detect electrical changes caused by the cardiac depolarization and repolarization during each cardiac cycle. In accordance with the instant disclosure the electrodes may be connected to the pulse generator 12 or may be formed on an outer surface thereof.

In accordance with a further aspect of the disclosure, the sensor 86 may be an EEG system from which the sleep stages of the patient may be determined. The EEG may include sensors implanted in the patient and operably connected to the pulse generator 12, either physically wires or via wireless communication protocols. Alternatively, the sensors may be implanted in the patient and operably connected to a satellite implanted device located above the shoulders of the patient and in communication with the pulse generator 12. Still further the sensors may be a wearable set of sensors that are in communication with the implantable device. Additionally or alternatively the EEG electrodes may communicate directly with the CTM 300.

Yet a further sensor 86 is a temperature sensor. It has been observed that patient's temperatures differ between a patient's sleeping temperature and their wakeful temperature. In addition, there are differences in temperature based on the sleep state of the patient. These too can be collected and assessed to determine a baseline for the patient, and to provide indicators of change of sleep state for the patient.

In view of inclusion of one or more of these sensors 50, sets of data can be constructed comparable what might be derived in a formal sleep study. For example, the total sleep time (TST) can be derived by comparing the time period that the patient (and INS 10) is in a lying down position, and the time where the motion sensor detects motion consistent with a sleeping heart rate or sleeping respiration. Once a TST is determined, a sleep efficiency can also be derived by comparing the TST to the total recording time (TRT) which may be the entirety of the period that the patient is in the lying down position.

Sleep stages, as in the case of a formal sleep study might require the use of EEG data from the EEG sensors, however, arousals or awakenings can be derived from the posture sensor either alone or in combination with the data from the blood-oxygen saturation sensor, or the respiration rate sensor. These would be instances where the patient transitioned from one to another posture and depending on the period of time between the beginning of the transition the transition can be characterized as an arousal or awakening. Gross motion data from a motion sensor, consistent with for example walking to the bathroom, or other data can also be overlaid on the data from the posture detector to assist in classifying the detected movements or change in posture as an awakening or an arousal.

Respiration rate may be sensed or derived by a number of methods. As noted above, a three-axis accelerometer may be tuned to the vibrations of the lungs. By such tuning the change in position of the sensor 86 can be plotted and normalized to provide a respiration rate for the patient. Further ECG data, as might be acquired from ECG sensors is known to be proportional to respiration rate. In this way as the ECG baseline shifts, as a result of increased heart rate, a proportion change in respiration rate can be determined. Similarly, an optical sensor, such as the reflectance blood-oxygen saturation sensor described above to measure blood-oxygen saturation levels may also be employed to determine a pulse transit time. A shift in this transit time is also known to be proportional with a chance in respiration rate. For both the ECG baseline and optical sensor baseline shifts, a normal range of both of these values for the patient while sleeping may be required to determine these changes in respiration rate.

With respect to the respiration rate, any or all of these respiration rate values measured or calculated above may be employed to develop an AHI value. The AHI is the number of apneas or hypopneas recorded during the study per hour of sleep. It is generally expressed as the number of events per hour. Based on the AHI, the severity of OSA is classified as follows in Table 1:

TABLE 2

| Severity | AHI Events |
|---|---|
| None/Minimal: | <5 per hour |
| Mild: | ≥5, but <15 per hour |
| Moderate: | ≥15, but <30 per hour |
| Severe: | ≥30 per hour |

By comparing changes in the lung vibration, and changes in the baseline of the ECG and pulse transit times, an initial approximation of instances of an apnea can be identified. When any of these occur, the blood-oxygen saturation level sensor can be triggered to record the blood-oxygen saturation level for a given period of time following the event (assuming it is not being constantly monitored). Where a change in respiration rate is observed, if it is followed by a drop in blood-oxygen saturation level, it can reasonably be identified as an apnea, as described above with respect to Table 2. As those are measured on any given night's sleep and over the course of days, weeks, and years the development of and the incidence of sleep apnea can be assessed and actively monitored by health care providers. In a similar fashion, a related value the respiratory disturbance index (RDI) can also be determined. RDI includes respiratory events called respiratory-effort related arousals (RERAs), which are arousals of the patient from sleep that do not met the standards of an apnea or a hypopnea but do disturb sleep. Thus, they may provide better insight into the quality of sleep of some patients. Though traditionally detected using esophageal manometry, the motion and sound sensors described above may be tuned to detect these events.

In accordance with a further aspect of the disclosure, when a stimulation pulse is not being delivered by an electrodes 30a-30d, the electrodes can be employed to detect the electrical potential of muscles. Electromyography (EMG) is a technique of evaluating and recording the electrical activity produced by skeletal muscles. An electromyograph detects the electrical potential generated by muscle cells when the cells are electrically or neurologically activated. In other examples, dedicated EMG sensing electrodes may be carried by housing 15 and/or lead body 22 and coupled to sensor 86 for EMG signal monitoring. EMG signal monitoring by control circuit 80 allows for detection of a low tonal state of the GG and/or GH muscles indicating a susceptibility to upper airway collapse. In one example, detection of a low tonal state of the protrusor muscles may be a trigger for delivering OSA therapy, particularly if combined with a detection of the pose of the patient indicating that they are in a reclined position. Thus, the EMG signals may be used by control circuit 80 for detecting a sleep state and/or low tonal state of the protrusor muscles for use in controlling therapy delivery circuit 84 for delivering stimulation pulses to cause protrusion of the patient's tongue.

EMG monitoring may further be used in monitoring for adequate protrusion and retraction or fatigue of the stimulated GG and/or GH muscles. If fatigue of the muscles is detected, control circuit 80 may alter to control the duty cycle, pulse amplitude and/or stimulating electrode vector of electrical stimulation pulse trains delivered by therapy delivery circuit 84 to minimize or avoid fatigue and/or allow adequate fatigue recovery time between duty cycle on times in accordance with the therapy delivery program. Further, based on the EMG signals, a determination can be made whether therapy is being prevented from delivery because one or more of the electrodes has moved relative to the muscles they are intended to stimulate.

Though described herein largely in the context of sensors 86 that form part of the INS 10, this instant disclosure is not so limited. As noted elsewhere one or more of the sensors including the EEG sensors, the leg movement sensors, the ECG sensor, the blood-oxygen saturation level sensor, and others may be external sensors 100 (FIG. 4) formed external to the patient and the INS 10 and in communication with either the INS 10 or the CTM 300 without departing from the scope of the disclosure.

Another aspect of the disclosure allows the patient to self-report certain data and the patient may periodically be requested to enter certain subjective data via the external programmer. This could include entering a rating of how tired they are after waking (e.g., on a scale of 1-10), hours slept, tiredness or soreness of the protrusor muscles on waking, how many times they believe they were aroused or awakened during the previous night's sleep, and other data related to their impression of the sleep and their therapy. These types of data provide a subjective sense of the therapy that can be compared and contrasted to the collected sensor data and computations made therefrom. In addition, the self-reported may include behavioral information such as eating, smoking, drinking alcohol, recreational and prescription drug use of the patient on the day prior to sleeping. From this behavioral data, additional determinations can be made. If for example the patient indicates that on a particular evening they consumed a large number of alcoholic beverages then the data collected from the following night's sleep may not be particularly insightful when analyzed later and may even skew the results if included in certain average statistics. Thus, they may be disregarded or at least discounted from the analysis of the overall sleep health of the patient.

All of the data being captured by the sensor 86 can be stored in memory 82 and transmitted via the telemetry circuit 86 to the CTM 300 and ultimately to the server 202, where the data may be included as part of the patient's electronic medical records (EMR) or another database of information that is available for analysis. The data may be assessed by a care provider at a remote computer 204 (FIG. 4) and adjustments may be made to the therapy delivery program. These adjustments may be adjustments to the amplitude of pulses, frequency of the pulses, the combination of electrodes 30a-30e and the order in which the combination is used to stimulate the protrusor muscles, the duty cycle of the electrodes and the pulses being applied and other factors to control the activation of the INS 10.

Further, this collected data from the sensor 86 may be analyzed and computations made to determine additional informative data such as total sleep time and sleep efficiency as well as values such as the AHI and RDI, hours per sleep stage, etc. This data may be used by the care provider to determine both the effectiveness and the efficiency of the therapy.

In accordance with one aspect of the disclosure, the data from the sensor 86 and the self-reported data, and the operational data of the INS 10 is analyzed at the server 202, and following a pre-defined protocol processed and a sleep score is determined. This sleep score, either alone, or in combination with some or all of the raw data or other computed values may be presented to the patient on the external programmer 50.

At the server 200, a variety of techniques and systems may be employed to automatically analyze the data being collected. These techniques may employ fuzzy logic or other data processing techniques to efficiently analyze the data and identify patterns for the particularly patient. The server 200 may further employ one or more neural networks or artificial intelligence (AI) engines. The AI engines can analyze the data from an individual patient and detect patterns in the data which can improve the efficiency of the patient's sleep and therewith their overall health. As an example, the AI can consider the EMG data from the patient and the blood-oxygen saturation levels of the patient, and correlate those data such that therapy is only delivered in those instances of low tonal state which are likely the result in an apnea. Further the therapy can be delivered only for as long as the patient might need to recover from that low tonal state. This analysis may include determining the amplitude, pulse width, frequency, electrodes for therapy, and other aspects directed at providing therapy to the patient. These patient-focused analyses can provide targeted therapy delivery programs for a particular individual improving the outcome for that patient.

In addition to analyzing the data derived from an individual to improve the outcome for the specific patient, the server 200 and any AI engine or other analytical tools included thereon or accessible therefrom can access the data of a larger population of patients. In one embodiment this population of patients includes all patients receiving a particular brand or model of INS 10. As can be appreciated, analyzing the volumes of data from all these patients can best be performed by automated and trained AI engines and neural networks. As above, the purpose is to identify patterns in the physiological data of the patients, the parameters or the therapy, and other data about the patients to find useful correlations that can be employed to adjust or modify the therapy delivery programs stored in memory 82 on the INS 10 and executed by the control circuit 80 and the therapy delivery circuit 84. By analyzing the global population data trends for patients with the INS 10 can be considered and global trends can be identified and utilized to modify the therapy delivery programs utilized in INS 10.

In one example of analyzing the global or at least a large population of data can provide useful in an initial set up of a therapy delivery program for a patient having a newly installed INS 10. An AI or other analytical tool can access some initial information regarding the individual patient. For example, the individual patient's height, weight, demographics, personal habits (smoking, drug use), co-morbidities (e.g., heart conditions, lung conditions), and if available sensor data and calculations derived therefrom as part of a sleep study. These data can then be compared to the global population for high correlations. These highly correlated patients in the global population each have their own therapy delivery program with which their therapy is delivered. These therapy delivery programs can then be analyzed in an effort to identify an initial therapy delivery program that will be beneficial to the individual patient whose INS 10 has only just been implanted. Similarly, the individual patient's therapy delivery program can be compared to the global population for a variety of factors. While ensuring that the patient's therapy delivery is consistent with his or her cohort of the global population might be one factor, a determination that they are not consistent might ultimately prove more important to developing potential changes to therapy delivery programs, particularly when the patient is experiencing highly efficient sleep of adequate duration with few apneic episodes. AI and neural networks are particularly adept at identifying these outliers in the data that are experiencing goods outcomes and utilizing them to adjust the therapy delivery programs to benefit the global population of sleep apnea patients.

In accordance with a further aspect of the disclosure, the CTM 300 may itself include an AI engine. For example, the AI 304 may be embodied on an NVIDIA GPU/Deep Learning chip set such as the NVIDIA EGX platform currently marketed by the NVIDIA Corporation or a similar product. By placing an AI 304 on the CTM 300, the burden of the patient specific data analysis (described above) can be shifted from the server 202 to the AI 304. In addition to the analysis aspects described above, the AI 304 in the CTM 300 can be in communication with the INS 10 at all times during therapy delivery. By being in communication with the INS 10 during therapy delivery, both the data related to therapy delivery (amplitude, frequency, pulse width, etc.) and the data from sensor 86. The AI 304 can then intervene in the therapy delivery for the patient as the therapy is being delivered if necessary to adjust the therapy parameters (e.g., amplitude, pulse width, frequency) or to stop therapy all together if there is an indication of the patient being awake or there is a detected failure of some component of the INS 10. The ceasing of stimulation due to awakening or arousal of the patient may only be transitory, and upon detection of the patient returning to a sleep state the AI 304 can cause the INS 10 to again begin therapy.

As an example, once the therapy is turned on using the external programmer 50, rather simply having a delay function, the AI 304 can monitor EMG signals and detect a loss of muscle tone of the protrusor muscles. While some loss of muscle tone is known to occur for all persons when sleeping, those suffering from sleep apnea have experience a greater loss of muscle tone. The AI 304 can monitor this EMG signal, compare that signal to historical data for the patient, and make determinations not just on whether to apply therapy to the patient, but the amount of therapy to be applied based on the received sensor data. Similarly, the AI 304 can be utilized to determine and adjust the parameters of the therapy based on the detected posture of the patient as described above.

By analyzing this data regarding when and how much therapy to apply to the patient a number of savings can be achieved. First, the patient does not receive more therapy than they actually require to address their sleep apnea. While the excess therapy is not dangerous to the patient, as noted elsewhere herein it can result in fatigue of the protrusor muscles which can be felt by the patient. In addition, the over application of therapy unnecessarily utilizes energy stored in the power source 90. Thus, the reduction on therapy application can reduce the power consumption (e.g., the burden on the power source 90).

Another aspect of the AI 304 is that it can perform all of the calculations described above with respect to the various sensor data received from the one or more sensors 86 described herein. In accordance with this aspect of the disclosure, the AI 304 can perform the calculations and present them to the patient in a user interface on the external programmer 50. This may include providing to the patient a sleep score that the patient can quickly review after waking for the day to assist them in understanding the effects of the therapy being delivered, as well as the amount of therapy delivered, and the number of interventional actions that the INS 10. As will be appreciated this data can also be transmitted to the server 200 and stored in the patient's EMR for review by applications operating on the server 200 including an AI or neural networks, and for presentation to a health care provider via a remote computer 204.

The AI 304 and the CTM 300 may have a regular communication interval, where the CTM 300 communicates with the patient programmer 50 to update information for display via the OSA App. in one or more user interfaces. The patient programmer 50 may also have a regular communication interval with the sever 200 to upload the data from the sensor 86 or the calculations made by the AI 304.

Both the AI 304 operating on the CTM 300 and any AI operating on the server 202 can analyze the data generated by the INS 10, and particularly the sensors 86 included therein, and generate alerts that can be sent to either the patient via the external programmer 50 and a user interface thereon and to the remote computer 204 where the alert can be reviewed and acted on by the health care provided. In one example, this may be in the form of an alarm that might sound on the external programmer 50 intended to wake the patient from sleeping in view of a detected condition. Other types of alerts and feedback can be delivered to the user interface on the external programmer 50 without departing from the scope of the disclosure.

The AI 304 may utilize the data provided by the sensors 86 and calculations made from that data to determine sleep architecture for the individual patient. This sleep architecture can be presented to the patient on one or more user interfaces. Among the items that might be displayed on the user interface is an indication of the integrity of the electrodes. As an example, the failure to detect an EMG signal can be an indicator of a failed electrode. Other items that may be displayed on the user interface as a part of the sleep architecture include information such as total hours of sleep, hours spent in each sleep stage, AHI values or RDI values, quality of sleep, efficiency of sleep, and other sleep related data. Additionally or alternatively, the user interface may present data regarding respiration rate, possibly in comparison to different sleep stages. In addition, the user interface may display information regarding the application of therapy. These data may include the amount of therapy, the number of times that a therapy has been initiated, and others. Further, the user interface can present data regarding about the quality or efficiency of the therapy. This may be presented in terms of the number of apnea's averted or treated to avoid arousals or awakenings as a comparison of the amount of therapy applied. Still further, this sleep architecture data can be presented in a form that allows for historical comparisons so that the patient or the health care provider can analyze the performance of the INS 10 and the effectiveness of any changes to the therapy delivery program and the interventions by the AI 304.

Those of ordinary skill in the art of sleep apnea and sleep studies will appreciate that any of the preceding sensed physiological data sensed by sensor 86, or calculated therefrom, and any of the stimulation data may be combined or compared to provide a variety of different analytical data points that can be analyzed by the AI 304, an AI or other analytical tools as accessible to the sever 202, and of course the health care provider via remote computer 204.

Figure 5:
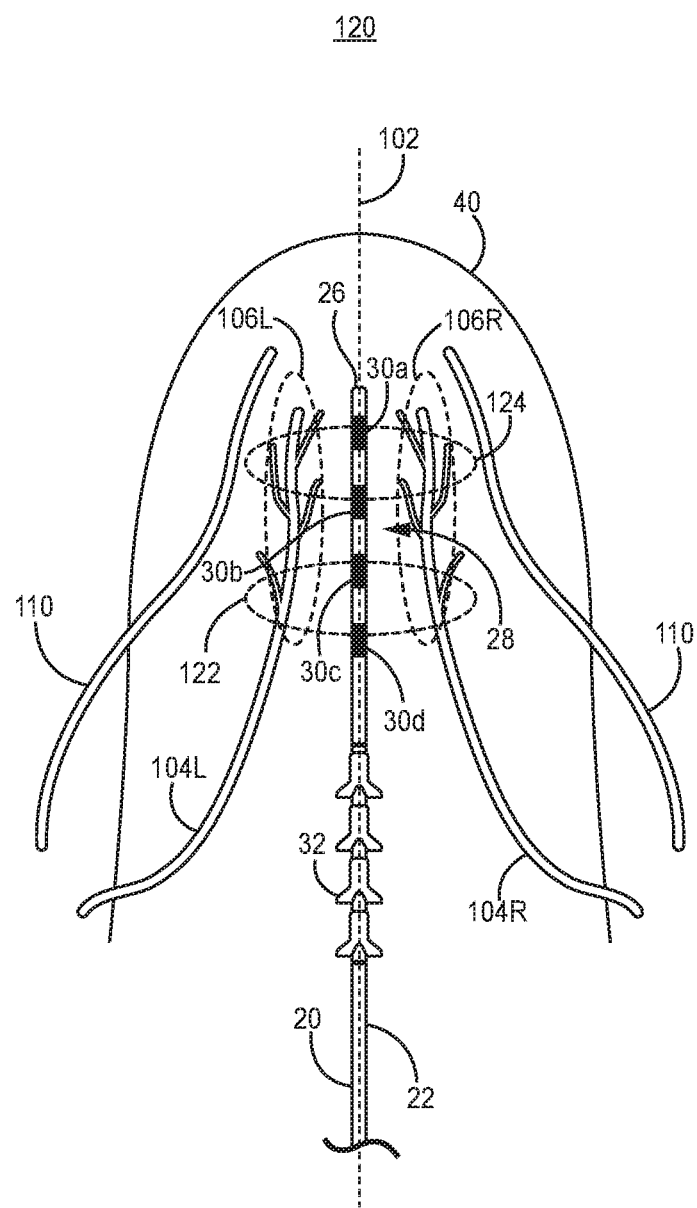
FIG. 5 is a diagram of the distal portion of the lead of the INS of FIG. 1 deployed for delivering OSA therapy according to one aspect of the disclosure.

While the preceding aspects of the disclosure have focused on aspects of the external programmer 50, the CTM 300 and the broader system (FIG. 4), the following description details the lead 20 and its placement as well as the electrical pulses and their application to the patient's tongue as part of a therapy delivery program. FIG. 5 depicts a single intramuscular lead 20 inserted into the tongue 40 of a patient. Lead 20 may include two or more electrodes, and in the example shown lead 20 includes four electrodes 30*a*, 30*b*, 30*c*, and 30*d* (collectively referred to as "electrodes 30") spaced apart longitudinally along lead body 22. Lead body 22 is a flexible lead body which may define one or more lumens within which insulated electrical conductors extend to a respective electrode 30*a*-30*d*. The distal most electrode 30*a* may be adjacent or proximate to lead distal end 26. Each of electrodes 30*b*, 30*c* and 30*d* are spaced proximally from the respective adjacent electrode 30*a*, 30*b* and 30*c* by a respective interelectrode distance.

Each electrode 30*a*-30*d* is shown have equivalent electrode lengths. In other examples, however, electrodes 30*a*-30*d* may have electrode lengths that are different from each other in order to optimize placement of the electrodes 30 or the resulting electrical field of stimulation relative to targeted stimulation sites corresponding to left and right portions of the HGN or branches thereof and/or motor points of the GG and GH muscles. The interelectrode spacings between electrodes 30a, 30b, 30c, and 30d are shown to be approximately equal in FIG. 5, however they may also be different from each other in order to optimize placement of electrodes 30 relative to the targeted stimulation sites or the resulting electrical field of stimulation relative to targeted stimulation sites corresponding to left and right hypoglossal nerves or branches of hypoglossal nerves and/or motor points of protrusor muscles 42a, 42, or 46.

In some examples, electrodes 30a and 30b form an anode and cathode pair for delivering bipolar stimulation in one portion of the protrusor muscles, e.g., either the left or right GG and/or GH muscles or either a proximal or distal portion of the GG and/or GH muscles. Electrodes 30c and 30d may form a second anode and cathode pair for delivering bipolar stimulation in a different portion of the protrusor muscles (e.g., the other of the left or right portions or the other of the proximal or distal portions). Accordingly, the interelectrode spacing between the two bipolar pairs 30a-30b and 30c-30d may be different than the interelectrode spacing and between the anode and cathode within each bipolar pair 30a-30b and 30c-30d.

In one example, the total distance encompassed by electrodes 30a-30d along the lead body 22 may be about 20 millimeter, 25 millimeters, or 30 millimeters as examples. In one example, the total distance is between 20 and 22 millimeters. The interelectrode spacings between a proximal electrode pair 30c-30d and a distal electrode pair 30a-30b, respectively, may be between 2 and 6 mm, including all integer values therebetween. The interelectrode spacing separating the distal and proximal pairs 30a-30b and 30c-30d may be the same or different from each other and the spacing between individual electrodes of any such pair.

In the example shown, each of electrodes 30a-30d is shown as a circumferential ring electrode which may be uniform in diameter with lead body 22. In other examples, electrodes 30 may include other types of electrodes such as a tip electrode, a helical electrode, a coil electrode, a segmented electrode, a button electrode as examples. For instance, the distal most electrode 30a may be provided as a tip electrode at the lead distal end 26 with the remaining three electrodes 30b, 30c and 30d being ring electrodes. When electrode 30a is positioned at the distal end 26, electrode 30a may be a helical electrode configured to screw into the muscle tissue at the implant site to additionally serve as a fixation member for anchoring the lead 20 at the targeted therapy delivery site. In other examples, one or more of electrodes 30a-d may be a hook electrode or barbed electrode to provide active fixation of the lead 20 at the therapy delivery site.

Lead 20 may include one or more fixation member 32 for minimizing the likelihood of lead migration. In the example shown, fixation member 32 includes multiple sets of tines which engage the surrounding tissue when lead 20 is positioned at the target therapy delivery site. The tines of fixation member 32 may extend radially and proximally at an angle relative to the longitudinal axis of lead body 22 to prevent or reduce retraction of lead body 22 in the proximal direction. Tines of fixation member 32 may be collapsible against lead body 22 when lead 20 is held within the confines of a lead delivery tool, e.g., a needle or introducer, used to deploy lead 20 at the target implant site. Upon removal of the lead delivery tool, the tines of fixation member 32 may spread to a normally extended position to engage with surrounding tissue and resist proximal and lateral migration of lead body 22. In other examples, fixation member 32 may include one or more hooks, barbs, helices, or other fixation mechanisms extending from one or more longitudinal locations along lead body 22 and/or lead distal end 26. Fixation member 32 may partially or wholly engage the GG, GH muscles and/or other muscles below the tongue, and/or other soft tissues of the neck, e.g., fat and connective tissue, when proximal end of lead body 20 is tunneled to an implant pocket of pulse generator 12. In other examples, fixation member 32 may include one or more fixation mechanisms located at other locations than the location shown in FIG. 5, including at or proximate to distal end 26, between electrodes 30, or otherwise more distally or more proximally than the location shown. The implant pocket of pulse generator 12 may be along the patient's neck (see FIG. 1), accordingly the length of the elongated lead body 22 from distal end 26 to the lead proximal end 24 (FIG. 1) may be selected to extend from the a target therapy delivery site in the protrusor muscles to a location along the patient's neck where the pulse generator 12 is implanted. This length may be up to 10 cm or up to 20 cm as examples but may generally be 25 cm or less, though longer or shorter lead body lengths may be used depending on the anatomy and size of the individual patient.

FIG. 5 further depicts the lead 20 deployed for delivering OSA therapy according to another example. In this example, lead 20 carrying electrodes 30 is advanced approximately along or parallel to midline 102 of tongue 40. In the example shown, lead body 22 is shown approximately centered along midline 102, however in other examples lead body 22 may be laterally offset from midline 102 in the left or right directions but is generally medial to both of the left HGN 104L and the right HGN 104R. The distal end 26 of lead 20 may be inserted inferiorly to the body of tongue 40, e.g., at a percutaneous insertion point along the submandibular triangle, in the musculature below the floor of the oral cavity. The distal end 26 is advanced to position electrodes 30 medially to the left and right HGNs 104L and 104R, e.g., approximately midway between the hyoid bone the mental protuberance (chin). An electrical field produced by stimulation pulses delivered between any bipolar pair of electrodes selected from electrodes 30 may encompass a portion of both the left target region 106L and the right target region 106R to produce bilateral stimulation of the HGNs 104L and 104R and therefore bilateral recruitment of the protrusor muscles. Bilateral recruitment of the protrusor muscles may provide greater airway opening than unilateral stimulation that is generally performed using a nerve cuff electrode along the HGN. For example, electrical stimulation pulses delivered using electrodes 30a and 30b may produce electrical field 122 (shown conceptually) encompassing a portion of both of the left and right target regions 106L and 106R. Electrical stimulation pulses delivered using electrodes 30c and 30d may produce electrical field 124 (shown conceptually) encompassing a portion of both of the left and right target regions 106L and 106R. The portions of the left and right target regions 106L and 106R encompassed by electrical field 122 are posterior portions relative the portions of the left and right target regions 106L and 106R encompassed by electrical field 124.

In some examples, electrical stimulation is delivered by pulse generator 12 by sequentially selecting different electrode pairs from among the available electrodes 30 to sequentially recruit different bilateral anterior and bilateral posterior portions of the HGNs 104L and 104R. This electrode selection may result in recruitment of different anterior and posterior portions of the protrusor muscles. The sequential selection of different electrode pairs may be overlapping or non-overlapping. The electrical stimulation is delivered throughout an extended time period encompassing multiple respiratory cycles independent of the timing of respiratory cycles to maintain a protruded state of tongue 40 from the beginning of the time period to the end of the time period. The electrodes 30 may be selected in bipolar pairs comprising the most distal pair 30a and 30b, the outermost pair 30a and 30d, the innermost pair 30b and 30c, the most proximal pair 30c and 30d or alternating electrodes along lead body 22, e.g., 30a and 30c or 30b and 30d. Sequential selection of two or more different electrode pairs allows for sequential recruitment of different portions of the protrusor muscles to reduce the likelihood of fatigue.

In some examples, electrical stimulation delivered using an electrode pair, e.g., 30a and 30b, that is relatively more distal along distal lead portion 28 and implanted relatively anteriorly along tongue 40 may recruit a greater portion of anterior muscle fibers, e.g., within the GG muscle. Electrical stimulation delivered using an electrode pair, e.g., 30c and 30d, that is relatively more proximal along distal lead portion 28 and implanted relatively posteriorly along tongue 40 may recruit a greater portion of posterior muscle fibers, e.g., within the GH muscle. Sequential selection of electrodes 30 for delivering electrical stimulation pulses allows sequential recruitment in overlapping or non-overlapping patterns of anterior and posterior portions of the protrusor muscles to sustain the tongue in a protruded state throughout the extended time period while reducing or avoiding muscle fatigue.

Figure 6:
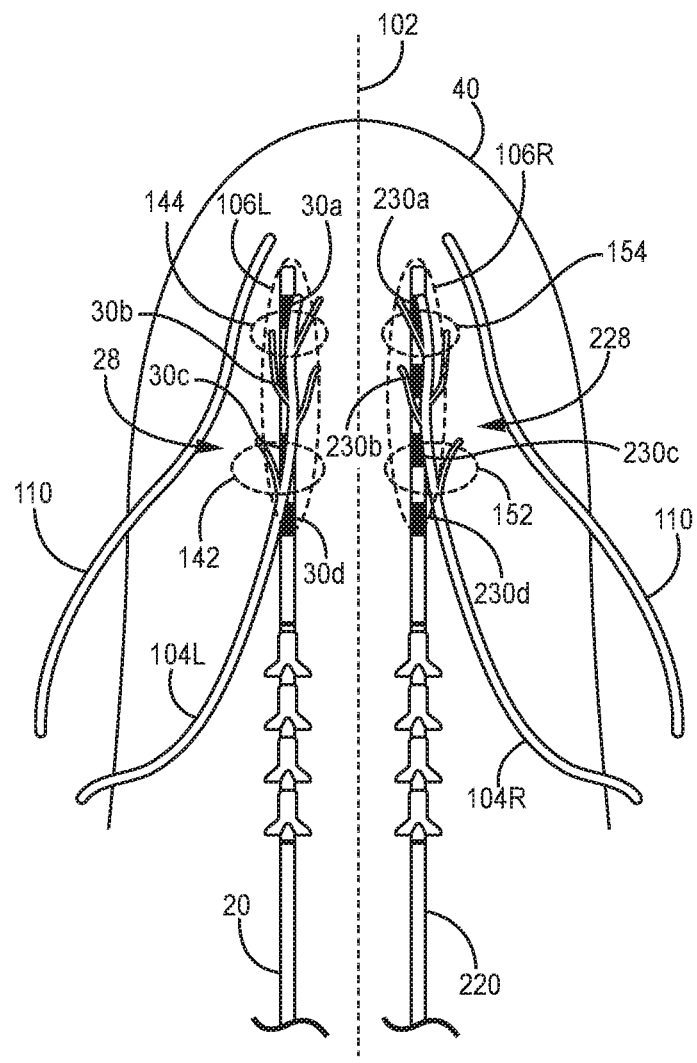
FIG. 6 is a diagram of the distal portion of a two lead INS deployed for delivering OSA therapy according to a further aspect of the disclosure.

FIG. 6 depicts the distal portion of a dual lead system for delivering OSA therapy. In this example, one lead 20 is advanced anteriorly approximately parallel to midline 102 and offset, e.g. by 5-8 millimeters to the left of midline 102, to position distal portion 28 and electrodes 30 in or adjacent to the left target region 106L. A second lead 220 is advanced anteriorly approximately parallel to midline 102 but offset laterally to the right of midline 102 to position distal portion 228 and electrodes 230 in or adjacent the right target region 106R. Lead 20 may be inserted from a left lateral or posterior approach of the body of tongue 40, and lead 230 may be inserted from a right lateral or posterior approach of the body of tongue 40. In other examples, both leads 20 and 220 may be inserted from only a left or only a right approach with one lead traversing midline 102 to position the electrodes 30 or 230 along the opposite side of midline 102 from the approaching side. Lead 20 and/or lead 220 may be advanced at an oblique angle relative to midline 102 but may not cross midline 102. In other examples, one or both leads 20 and 220 may approach and cross midline 102 at an oblique angle such that one or both of distal portions 28 and 228 extend in or adjacent to both the right and left target regions 106L and 106R.

In the example shown, relatively more localized control of the recruitment of left, right, anterior and posterior portions of the protrusor muscles may be achieve by selecting different electrode pairs from among the electrodes 30a through 30d and 230a through 230d. For example, any combination of electrodes 30a through 30d may be selected for delivering electrical stimulation pulses to the left portions of the protrusor muscles. More distal electrodes 30a and 30b may be selected for stimulation of more anterior portions of the left protrusor muscles (corresponding to electrical field 144) and more proximal electrodes 30c and 30d may be selected for stimulation of more posterior portions of the left protrusor muscles (corresponding to electrical field 142). Any combination of electrodes 230a through 230d may be selected for delivering electrical stimulation pulses to the right portions of the protrusor muscles. More distal electrodes 230a and 230b may be selected for stimulation of more anterior portions of the right protrusor muscles (corresponding to electrical field 154) and more proximal electrodes 230c and 230d may be selected for stimulation of more posterior portions of the right protrusor muscles (corresponding to electrical field 152).

Switching circuit 96 (FIG. 2) may be configured to select electrode pairs that include one electrode on one of leads 20 or 220 and another electrode on the other lead 20 or 220 to produce an electrical field (not shown) that encompasses portions of both the left target region 106L and the right target region 106R simultaneously for bilateral stimulation. Any combination of the available electrodes 30a through 30d and electrodes 230a through 230d may be selected as two or more bipolar pairs, which are selected in a repeated, sequential pattern to sequentially recruit different portions of the two target regions 106L and 106R. The sequential selection of electrode pairs may be overlapping or non-overlapping, but electrical stimulation pulses are delivered without interruption at one or more selected frequencies throughout an extended time period to maintain tongue 40 in a protruded state from the beginning of the time period to the end of the time period, encompassing multiple respiratory cycles.

In the example of FIG. 6 including two leads, two pairs of electrodes may be selected simultaneously and sequentially with one or more other pairs of electrodes. For example, electrodes 30a and 30b may be selected as one bipolar pair and electrodes 230c and 230d may be selected as a second bipolar pair for simultaneous stimulation of the left, anterior portion of the target region 106L and the right posterior portion of the target region 106R. The electrodes 30c and 30d may be selected as the next bipolar pair from lead 20, simultaneously with electrodes 230a and 230b selected as the next bipolar pair from lead 220. In this way, electrical stimulation may be delivered bilaterally, alternating between posterior and anterior regions on each side. The anterior left (30a and 30b) and posterior right (230c and 230d) bipolar pairs may be selected first, and the posterior left (30c and 30d) and anterior right (230a and 230b) bipolar pairs may be selected second in a repeated, alternating fashion to maintain tongue 40 in a protruded state continuously during an extended time period encompassing multiple respiratory cycles. In other examples, both of the anterior pairs (30a-30b and 230a-230b) may be selected simultaneously first, and both the posterior pairs (30c-30d and 230c-230d) may be selected simultaneously second, sequentially following the anterior pairs. In this way, continuous bilateral stimulation may be achieved while sequentially alternating between posterior and anterior portions to avoid or reduce fatigue. In contrast to other OSA therapy systems that rely on a sensor for sensing the inspiratory phase of respiration to coordinate the therapy with the inspiratory phase, the intramuscular electrodes 30 positioned to stimulate different portions of the protrusor muscles do not require synchronization to the respiratory cycle. Alternation of stimulation locations within the protrusor muscles allows different portions of the muscles to rest while other portions are activated to avoid collapse of the tongue against the upper airway while also avoiding muscle fatigue.

It is to be understood that more or fewer than the four electrodes shown in the examples presented herein may be included along the distal portion of a lead used in conjunction with the OSA therapy techniques disclosed herein. A lead carrying multiple electrodes for delivering OSA therapy may include 2, 3, 5, 6 or other selected number of electrodes. When the lead includes only two electrodes, a second lead having at least one electrode may be included to provide at least two different bipolar electrode pairs for sequential stimulation of different portions of the right and/or left medial HGNs. Furthermore, while the selected electrode pairs are generally referred to herein as "bipolar pair" including one cathode and one return anode, it is recognized that three or more electrodes may be selected at a time to provide desired electrical field or stimulation vector for recruiting a desired portion of the protrusor muscles. Accordingly, the cathode of a bipolar "pair" may include one or more electrodes selected simultaneously from the available electrodes and/or the anode of the bipolar "pair" may include one or more electrodes selected simultaneously from the available electrodes.

Figure 7:
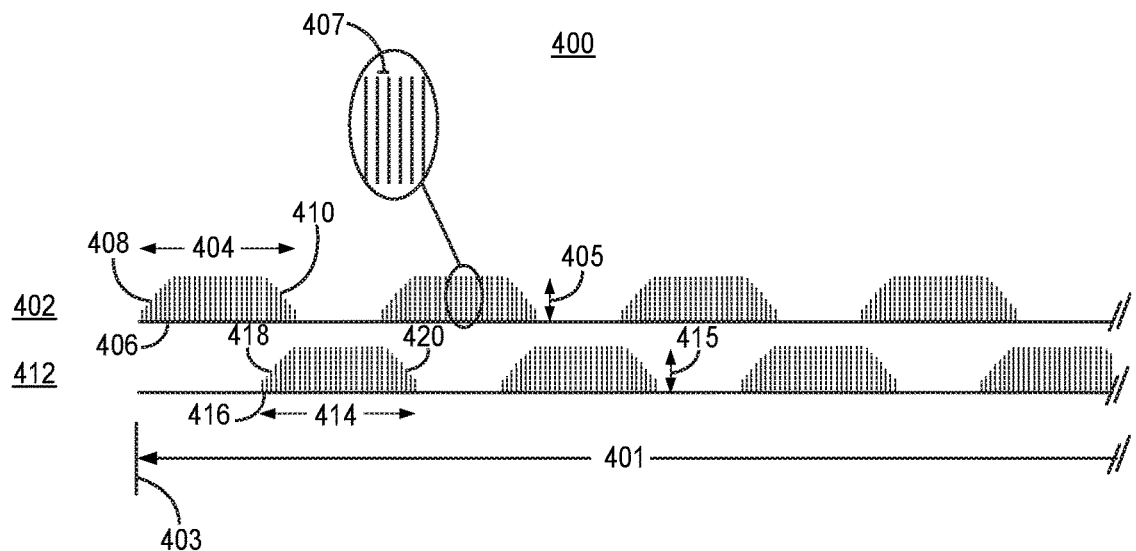
FIG. 7 timing diagram illustrating a method performed by the system of FIG. 1 for delivering selective stimulation to the protrusor muscles for promoting upper airway patency during sleep according to one example.

FIG. 7 timing diagram illustrating a method performed by pulse generator 12 for delivering selective stimulation to the protrusor muscles for promoting upper airway patency during sleep according to one example. Electrical stimulation is delivered over a therapy time period 401 having a starting time 403 and an ending time (not shown). Electrical stimulation pulses that are delivered when pulse generator sequentially selects a first bipolar electrode pair 402 and a second bipolar electrode pair 412 in an alternating, repeating manner are shown. The first and second bipolar electrode pairs 402 and 412 may correspond to any two different electrode pairs described in the examples above in conjunction with FIGS. 5-6.

A first train of electrical pulses 406 is shown starting at the onset 403 or therapy time period 401. The first train of electrical pulses 406 is delivered using bipolar electrode pair 402 for a duty cycle time interval 404. The first train of electrical pulses 406 has a pulse amplitude 405 and pulse frequency, e.g., 20 to 50 Hz, defined by the interpulse intervals 407. The first train of electrical pulses 406, also referred to as "pulse train" 406, may have a ramp on portion 408 during which the pulse amplitude is gradually increased from a starting voltage amplitude up to pulse voltage amplitude 405. In other examples, the pulse width may be gradually increased. In this way the delivered pulse energy is gradually increased to promote a gentle transition from the relaxed, non-stimulated state to the protruded state of the tongue.

The train of electrical pulses 406 may include a ramp off portion 410 during which the pulse amplitude (and/or pulse width) is decremented from the pulse voltage amplitude 405 to an ending amplitude at the expiration of the duty cycle time interval 404. In other examples, pulse train 406 may include a ramp on portion 408 and no ramp off portion 410. In this case, the last pulse of pulse train 406 delivered at the expiration of duty cycle time interval 404 may be delivered at the full pulse voltage amplitude 405. Upon expiration of the duty cycle time interval 404, electrical stimulation delivery via bipolar electrode pair 402 is terminated.

In the example shown, a second electrode pair 412 is selected when of duty cycle time interval 404 is expiring. The second electrode pair 412 may be selected such that delivery of electrical stimulation pulse train 416 starts a ramp on portion 418 that is simultaneous with the ramp of portion 410 of train 406. In other examples, the ramp on portion 418 of pulse train 416 may start at the expiration of the first duty cycle time interval 404. When pulse train 406 does not include a ramp off portion 410, the pulse train 416 may be started such that the ramp on portion 418 ends just before, just after or coincidentally with the expiration of duty cycle time interval 404. The second pulse train 416 has a duration of duty cycle time interval 414 and may end with an optional ramp off portion 420, which may overlap with the ramp on portion of the next pulse train delivered using the first electrode pair 402.

In this example, pulse trains 406 and 416 are shown to be equivalent in amplitude 405 and 415, pulse width, pulse frequency (and inter pulse interval 407), and duty cycle time interval 404 and 414. It is contemplated, however, that each of the stimulation control parameters used to control delivery of the sequential pulse trains 406 and 416 may be separately controlled and set to different values as needed to achieve a desired sustained protrusion of tongue 40 while avoiding or minimizing fatigue.

The sequential pulse trains 406 and 416 are delivered using two different electrode pairs 402 and 412 such that different portions of the protrusor muscles are recruited by the pulse trains 406 and 416 allowing one portion to rest while the other is being stimulated. However, pulse trains 404 and 406 occur in a sequential overlapping or non-overlapping manner such that electrical pulses are delivered at one or more selected frequencies for the entire duration of the therapy time period 401 to sustain the tongue in a protruded state throughout time period 401. It is to be understood that the relative down and/or forward position of the protruded tongue may shift or change as different electrode pairs are selected but the tongue remains in a protruded state throughout therapy time period 401.

At times, the pulse trains 404 and 406 may be overlapping to simultaneously recruit the left and right GG and/or GH muscles to create a relatively greater force (compared to recruitment of a single side) to pull the tongue forward to open an obstructed upper airway. As described generally above, the overlapping pulse trains 404 and 406 may cause temporary fatigue of the protrusor muscles along the left or right side but the temporary fatigue may improve the therapy effectiveness to ensure an open upper airway during an apneic episode. Recovery from fatigue will occur between duty cycles and at the end of an apneic episode. Duty cycle lengths may vary between patients depending on the fatigue properties of the individual patient. Control circuit 80 (FIG. 2) may control the duty cycle on time in a manner that minimizes or avoids fatigue in a closed loop system using a signal from sensor 86, e.g., a motion sensor signal and or EMG signal correlated protrusor muscle contraction force and subsequent fatigue.

Figure 8:
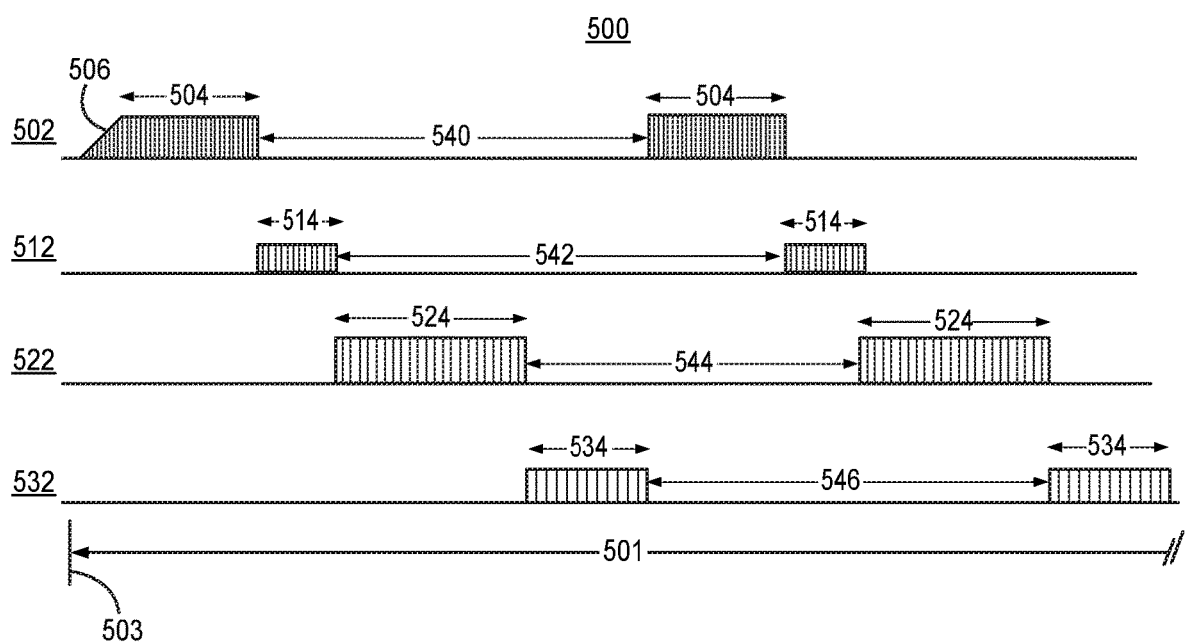
FIG. 8 is a timing diagram of a method for delivering OSA therapy by the system of FIG. 1 according to another example.

FIG. 8 is a timing diagram 500 of a method for delivering OSA therapy by pulse generator 12 according to another example. In this example, a therapy delivery time period 501 is started at 503 with a ramp on interval 506 delivered using a first bipolar electrode pair 502. The ramp on interval 506 is followed by a duty cycle time interval 504. Upon expiration of the duty cycle time interval 504, a second bipolar electrode pair 512 is selected for delivering electrical stimulation pulses for a second duty cycle time interval 514. A third duty cycle time interval 524 starts upon the expiration of the second duty cycle time interval 514, and stimulation pulses are delivered by selecting a third bipolar electrode pair 522 different than the first two pairs 502 and 512. A fourth bipolar pair 532 is selected upon expiration of the third duty cycle time interval 524 and used to deliver stimulation pulses over the fourth duty cycle time interval 534. Upon expiration of the fourth duty cycle time interval 534, the sequence is repeated beginning with duty cycle time interval 504 again.

In this example, four different bipolar pairs are selected in sequence. The four different bipolar electrode pairs may differ by at least one electrode and/or the polarity of another bipolar electrode pair. For example, when a single quadripolar lead 20 is used, the four bipolar pairs may include 30a-30b, 30b-30c, 30c-30d and 30a-30d. The portions of the protrusor muscles recruited by the four different pairs may not be mutually exclusive since the electrical fields of the four different pairs may stimulate some of the same nerve fibers. Four different portions of the protrusor muscles may be recruited, which may include overlapping portions. The relatively long recovery periods 540, 542, 544 and 546 between respective duty cycle time intervals allows each different portion of the protrusor muscles to recover before the next duty cycle. When recruited muscle portions overlap between selected electrode pairs, the bipolar electrode pairs may be selected in a sequence that avoids stimulating the overlapping recruited muscle portions consecutively. All recruited muscle portions are allowed to recover during at least a portion of each respective recovery period 540, 542, 544 and/or 546. For example, if the bipolar electrode pair 502 and the bipolar electrode pair 522 recruit overlapping portions of the protrusor muscles, the recruited portions may still recover during the second duty cycle time interval 514 and during the fourth duty cycle time interval 534.

The duration of each duty cycle time interval, 504, 514, 524 and 534, may be the same or different from each other, resulting in the same or different overall duty cycles. For example, when four bipolar electrode pairs are sequentially selected, stimulation delivery for each individual pair may be a 25% duty cycle. In other examples, a combination of different duty cycles, e.g., 30%, 10%, 40% and 20%, could be selected in order to promote sustained protrusion of the tongue with adequate airway opening while minimizing or avoiding fatigue. The selection of duty cycle may depend on the particular muscles or muscle portions being recruited and the associated response (position) of the tongue to the stimulation for a given electrode pair selection.

The stimulation control parameters used during each of the duty cycle time intervals 504, 514, 524, and 534 for delivering electrical pulses using each of the different bipolar electrode pairs 502, 512, 522 and 532 may be the same or different. As shown, a different pulse voltage amplitude and a different interpulse interval and resulting pulse train frequency may be used. The pulse amplitude, pulse width, pulse frequency, pulse shape or other pulse control parameters may be controlled according to settings selected for each bipolar electrode pair.

In the example shown, one ramp on portion 506 of the stimulation protocol is shown at the onset of the therapy delivery time period 501. Once the stimulation is ramped up to position the tongue in a protruded position, no other subsequent duty cycle time intervals 504 (other than the first one), 514, 524 and 534 may include or be proceeded by a ramp on portion. In other examples, a ramp on portion may precede each duty cycle time interval (or be included in the duty cycle time interval as shown in FIG. 7) and may overlap with the preceding duty cycle time interval. No ramp off portions are shown in the example of FIG. 8. In other examples, ramp off portions may follow or be included in each duty cycle time interval 504, 514, 524 and 534 and may overlap with the onset of the next duty cycle time interval as shown in FIG. 5. In some examples, only the last duty cycle time interval (not shown in FIG. 8) may include or be immediately followed by a ramp off portion to gently allow the tongue to return to a relaxed position at the end of the therapy delivery time period 501.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit for purposes of clarity, it should be understood that the techniques of this disclosure may be performed by a combination of units or modules associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an implantable medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

We claim:

1. An implantable neurostimulator (INS) system comprising:
   an electrical lead having formed thereon a pair of bipolar electrodes, wherein the electrical lead is configured for percutaneous implantation and placement of the pair of bipolar electrodes proximate, and without attaching, to one or more nerves of at least one of a genioglossus muscle or a geniohyoid muscle, which form protrusor muscles within a tongue, and proximate to one or more motor points of the protrusor muscles of a patient, and the electrical lead includes one or more electrodes configured to sense an electromyograph (EMG) proximate the protrusor muscles within the tongue;
   a pulse generator electrically connected to the electrical lead and configured to deliver electrical energy to the pair of bipolar electrodes, the pulse generator comprising a housing, the housing enclosing a sensor configured to detect one or more physiological parameters, a memory, a control circuit, and a telemetry circuit;
   a communications telemetry module (CTM) in communication with the telemetry circuit and configured to receive data collected by the sensor and data related to the delivery of electrical energy to the bipolar electrodes;
   an external programmer in communication with the CTM and configured to display a user interface that includes one or more of the data collected by the sensor and the data related to the delivery of the electrical energy to the bipolar electrodes; and processing circuitry configured to execute an artificial intelligence (AI) engine, wherein the AI engine is configured to analyze data of the sensed EMG to:
 determine a tonal state of at least one of the genioglossus muscle or the geniohyoid muscle that form the protrusor muscles within the tongue of the patient,
 determine an instance where the tonal state of at least one of the genioglossus muscle or the geniohyoid muscle is a low tonal state, based on the sensed EMG, and an apnea is likely to occur, based on the data collected by the sensor, and
 control a timing of when the electrical energy is delivered by the pulse generator based on the determined instance.

2. The system of claim 1, wherein the user interface displayed on the external programmer is configured to receive an input from a user to initiate therapy delivery.

3. The system of claim 1, wherein the user interface displayed on the external programmer is configured to display an amount of therapy delivered by the electrodes.

4. The system of claim 1, wherein the AI engine is configured to analyze the data related to the delivery of the electrical energy to the bipolar electrodes.

5. The system of claim 1, wherein to adjust the electrical energy delivered by the pulse generator, the AI engine is configured to adjust a therapy delivery program stored in the memory for the delivery of the electrical energy to the bipolar electrodes.

6. The system of claim 2, wherein the data collected by the sensor includes one or more of motion data, heart rate data, electrocardiogram data, respiration rate data, blood-oxygen saturation data or posture data.

7. The system of claim 6, wherein the AI engine is configured to calculate one or more of an Apnea-Hypopnea Index (AHI) value, a Respiration Disturbance Index (RDI) value, total sleep time, sleep efficiency value, power consumption value, or therapeutic efficiency.

8. The system of claim 1, further comprising one or more external sensors in communication with the CTM.

9. The system of claim 1, further comprising a server in communication with the external programmer or an external sensor, and configured to receive one or more of the data collected by the sensor, the data of the sensed EMG, the data related to the delivery of the electrical energy to the bipolar electrodes, and the data collected by the external sensor.

10. The system of claim 9, wherein one or more of the data collected by the sensor, the data of the sensed EMG, the data related to the delivery of the electrical energy to the bipolar electrodes, and the data collected by the external sensor are stored in an electronic medical record (EMR) for the patient.

11. The system of claim 10, wherein the AI engine is configured to access the EMR and analyze the data contained therein to update a therapy delivery program for the delivery of the electrical energy to the bipolar electrodes.

12. The system of claim 11, wherein the sensor data stored in the EMR includes one or more of motion data, heart rate data, electrocardiogram data, respiration rate data, electromyograph data, blood-oxygen saturation data or posture data.

13. The system of claim 12, wherein the AI engine is configured to calculate one or more of an Apnea-Hypopnea Index (AHI) value, a Respiration Disturbance Index (RDI) value, total sleep time, sleep efficiency value, power consumption value, or therapeutic efficiency.

14. The system of claim 11, wherein the server is configured to communicate the updated therapy delivery program to the external programmer, and the external programmer is configured to communicate the updated therapy delivery program to the memory of the pulse generator.

15. The system of claim 11, further comprising a remote computer in communication with the server, wherein the remote computer includes a user interface displaying one or more of the data collected by the sensor, the data of the sensed EMG, the data related to the delivery of the electrical energy to the bipolar electrodes, and the data collected by the external sensor.

16. The system of claim 15, wherein the remote computer is configured to receive and permit review of the updated therapy delivery program.

17. The system of claim 11, wherein the AI engine has access to EMR data of a larger population of patients.

18. The system of claim 17, wherein the AI engine is configured to analyze the EMR data of the larger population and identify one or more parameters for adjustment in a therapy delivery program for the delivery of the electrical energy to the pair of bipolar electrodes, the therapy delivery program being stored in the memory in the pulse generator.

* * * * *